(12) United States Patent
Bankston et al.

(10) Patent No.: US 7,645,878 B2
(45) Date of Patent: Jan. 12, 2010

(54) PROCESS FOR PREPARING QUINAZOLINE RHO-KINASE INHIBITORS AND INTERMEDIATES THEREOF

(75) Inventors: Donald Bankston, Wallingford, CT (US); Dhanaphalan Nagarathnam, Bethany, CT (US); Davoud Asgari, Plainsboro, NJ (US); Jianxing Shao, Cheshire, CT (US); Xiao-Gao Liu, New Haven, CT (US); Uday Khire, Hamden, CT (US); Chunguang Wang, Hamden, CT (US); Barry Hart, Woodbridge, CT (US); Stephen Boyer, Fairfield, CT (US); Olaf Weber, Woodbridge, CT (US); Mark Lynch, Madison, CT (US)

(73) Assignee: Bayer Healthcare LLC, Tarrytown, NY (US)

( * ) Notice: Subject to any disclaimer, the term of this patent is extended or adjusted under 35 U.S.C. 154(b) by 1264 days.

(21) Appl. No.: 10/252,369

(22) Filed: Sep. 24, 2002

(65) Prior Publication Data

US 2003/0220357 A1 Nov. 27, 2003

(51) Int. Cl.
*C07D 239/94* (2006.01)
(52) U.S. Cl. .............................. 544/284; 544/28; 544/79
(58) Field of Classification Search ............ 514/266.23; 544/284, 287
See application file for complete search history.

(56) References Cited

U.S. PATENT DOCUMENTS

| | | | | |
|---|---|---|---|---|
| 5,714,493 A | * | 2/1998 | Myers et al. | 514/262.1 |
| 6,184,226 B1 | * | 2/2001 | Chakravarty et al. | 514/266.22 |
| 6,218,410 B1 | | 4/2001 | Uehata et al. | 514/352 |
| 6,277,989 B1 | * | 8/2001 | Chakravarty et al. | 544/393 |
| 6,326,373 B1 | | 12/2001 | Uckun et al. | 514/266.1 |
| 6,391,874 B1 | | 5/2002 | Cockerill et al. | 514/233.5 |
| 2001/0044442 A1 | | 11/2001 | Uckun et al. | 514/259 |
| 2002/0055514 A1 | | 5/2002 | Uckun et al. | 514/259 |
| 2003/0087919 A1 | * | 5/2003 | Nagarathnam et al. | 514/266.23 |
| 2003/0125344 A1 | * | 7/2003 | Nagarathnam et al. | 514/266.2 |

FOREIGN PATENT DOCUMENTS

| | | |
|---|---|---|
| EP | 1 034 793 A1 | 9/2000 |
| EP | 1 163 910 A1 | 12/2001 |
| EP | 1 174 150 A1 | 1/2002 |
| EP | 1 177 796 A1 | 2/2002 |
| WO | WO 97/03069 A1 | 1/1997 |
| WO | WO 98/02434 A1 | 1/1998 |
| WO | WO 02/24667 A1 | 3/2002 |
| WO | WO 02/30465 A2 | 4/2002 |
| WO | WO 02/053143 A2 | 7/2002 |

* cited by examiner

*Primary Examiner*—James O Wilson
*Assistant Examiner*—Tamthom N Truong
(74) *Attorney, Agent, or Firm*—Millen, White, Zelano, Branigan, P.C.

(57) ABSTRACT

A process for the preparation of various quinazoline compounds which are useful as Rho-Kinase inhibitors, and thus having utility in the treatment of hypertension and other indications.

1 Claim, No Drawings

PROCESS FOR PREPARING QUINAZOLINE RHO-KINASE INHIBITORS AND INTERMEDIATES THEREOF

This application claims the benefit of the filing date of U.S. application Ser. No. 10/103,566 filed Mar. 22, 2002 and PCT Application No. PCT/US02/08659 filed Mar. 22, 2002.

FIELD OF THE INVENTION

The present invention relates to methods of producing quinazoline compounds and derivatives thereof which are useful as Rho-kinase Inhibitors or intermediates thereof. Rho-kinase inhibitors are useful for inhibiting tumor growth, treating erectile dysfunction, and treating other indications mediated by Rho-kinase, e.g., coronary heart disease.

BACKGROUND

The pathology of a number of human and animal diseases including hypertension, erectile dysfunction, coronary cerebral circulatory impairments, neurodegenerative disorders and cancer can be linked directly to changes in the actin cytoskeleton. These diseases pose a serious unmet medical need. The actin cytoskeleton is composed of a meshwork of actin filaments and actin-binding proteins found in all eukaryotic cells. In smooth muscle cells the assembly and disassembly of the actin cytoskeleton is the primary motor force responsible for smooth muscle contraction and relaxation. In non-muscle cells, dynamic rearrangements of the actin cytoskeleton are responsible for regulating cell morphology, cell motility, actin stress fiber formation, cell adhesion and specialized cellular functions such as neurite retraction, phagocytosis or cytokinesis (Van Aelst, et al. *Genes Dev* 1997, 11, 2295).

The actin cytoskeleton is controlled by a family of proteins that are a subset of the Ras superfamily of GTPases. This subset currently consists of RhoA through E and RhoG (refereed to collectively as Rho), Rac 1 and 2, Cdc42Hs and G25K and TC10 isoforms (Mackay, et al. *J Biol Chem* 1998, 273, 20685). These proteins are GTP (guanine nucleotide triphosphate) binding proteins with intrinsic GTPase activity. They act as molecular switches and cycles between inactive GDP (guanine nucleotide diphosphate) bound and active GTP bound states. Using biochemical and genetic manipulations, it has been possible to assign functions to each family member. Upon activation the Rho proteins controls the formation of actin stress fibers, thick bundles of actin filaments, and the clustering of integrins at focal adhesion complexes. When activated the Rac proteins control the formation of lamellopodia or membrane ruffles on the cell surface and Cdc42 controls filopodia formation. Together this family of proteins plays a critical part in the control of key cellular functions including cell movement, axonal guidance, cytokinesis, and changes in cell morphology, shape and polarity.

Depending on the cell type and the activating receptor, the Rho proteins can control different biological responses. In smooth muscle cells, Rho proteins are responsible for the calcium sensitization during smooth muscle contraction. In non-smooth muscle cells the Rho GTPases are responsible for the cellular responses to agonist such as lysophosphatidic acid (LPA), thrombin and thromboxane $A_2$ (Fukata, et al. *Trends Pharcol Sci* 2001, 22, 32). Agonist response is coupled through heterotrimeric G proteins $G_{alpha12}$ or $G_{alpha13}$ (Goetzl, et al. *Cancer Res* 1999, 59, 4732; Buhl, et al. *J Biol Chem* 1995, 270, 24631) though other receptors may be involved. Upon activation Rho GTPases activate a number of downstream effectors including PIP5-kinase, Rhothekin, Rhophilin, PKN and Rho kinase isoforms ROCK-1/ROKbeta and ROCK-1/ROKalpha (Mackay and Hall *J Biol Chem* 1998, 273, 20685; Aspenstrom *Curr Opin Cell Biol* 1999, 11, 95; Amano, et al. *Exp Cell Res* 2000, 261, 44).

Rho kinase was identified as a RhoA interacting protein isolated from bovine brain (Matsui, et al. *Embo J* 1996, 15, 2208). It is a member of the myotonic dystrophy family of protein kinase and contains a serine/threonine kinase domain at the amino terminus, a coiled-coil domain in the central region and a Rho interaction domain at the carboxy terminus (Amano, et al. *Exp Cell Res* 2000, 261, 44). Its kinase activity is enhanced upon binding to GTP-bound RhoA and when introduced into cells, it can reproduce many of the activities of activated RhoA. In smooth muscle cells Rho kinase mediates calcium sensitization and smooth muscle contraction and inhibition of Rho kinase blocks 5-HT and phenylephrine agonist induced muscle contraction. When introduced into non-smooth muscle cells, Rho kinase induces stress fiber formation and is required for the cellular transformation mediated by RhoA (Sahai, et al. *Curr Biol* 1999, 9, 136). Rho kinase regulates a number of downstream proteins through phosphorylation, including myosin light chain (Somlyo, et al. *J Physiol* (*Lond*) 2000, 522 Pt 2, 177), the myosin light chain phosphatase binding subunit (Fukata, et al. *J Cell Biol* 1998, 141, 409) and LIM-kinase 2 (Sumi, et al. *J Bio Chem* 2001, 276, 670).

Inhibition of Rho kinase activity in animal models has demonstrated a number of benefits of Rho kinase inhibitors for the treatment of human diseases. Several patents have appeared claiming (+)-trans-4-(1-aminoethyl)-1-(pyridin-4-ylaminocarbonyl)cyclohexane dihydrochloride monohydrate (WO-00078351, WO-00057913) and substituted isoquinolinesulfonyl (EP-00187371) compounds as Rho kinase inhibitors with activity in animal models. These include models of cardiovascular diseases such as hypertension (Uehata, et al. *Nature* 1997, 389, 990), atherosclerosis (Retzer, et al. *FEBS Lett* 2000, 466, 70), restenosis (Eto, et al. *Am J Physiol Heart Circ Physiol* 2000, 278, H1744; Negoro, et al. *Biochem Biophys Res Commun* 1999, 262, 211), cerebral ischemia (Uehata, et al. *Nature* 1997, 389, 990; Seasholtz, et al. *Circ Res* 1999, 84, 1186; Hitomi, et al. *Life Sci* 2000, 67, 1929; Yamamoto, et al. *J Cardiovasc Pharmacol* 2000, 35, 203), cerebral vasospasm (Sato, et al. *Circ Res* 2000, 87, 195; Kim, et al. *Neurosurgery* 2000, 46, 440), penile erectile dysfunction (Chitaley, et al. *Nat Med* 2001, 7, 119), central nervous system disorders such as neuronal degeneration and spinal cord injury (Hara, et al. *J Neurosurg* 2000, 93, 94; Toshima, et al. *Stroke* 2000, 31, 2245) and in neoplasias where inhibition of Rho kinase has been shown to inhibit tumor cell growth and metastasis (Itoh, et al. *Nat Med* 1999, 5, 221; Somlyo, et al. *Biochem Biophys Res Commun* 2000, 269, 652), angiogenesis (Uchida, et al. *Biochem Biophys Res Commun* 2000, 269, 633; Gingras, et al. *Biochem J* 2000, 348 Pt 2, 273), arterial thrombotic disorders such as platelet aggregation (Klages, et al. *J Cell Biol* 1999, 144, 745; Retzer, et al. *Cell Signal* 2000, 12, 645) and leukocyte aggregation (Kawaguchi, et al. *Eur J Pharmacol* 2000, 403, 203; Sanchez-Madrid, et al. *Embo J* 1999, 18, 501), asthma (Setoguchi, et al. *Br J Pharmacol* 2001, 132, 111; Nakahara, et al. *Eur J Pharmacol* 2000, 389, 103), regulation of intraoccular pressure (Honjo, et al. *Invest Ophthalmol Vis Sci* 2001, 42, 137) and bone resorption (Chellaiah, et al. *J Biol Chem* 2000, 275, 11993; Zhang, et al. *J Cell Sci* 1995, 108, 2285).

The inhibition of Rho kinase activity in patients has benefits for controlling cerebral vasospasms and ischemia following subarachnoid hemorrhage (*Pharma Japan* 1995, 1470, 16).

SUMMARY OF THE INVENTION

The present invention provides methods of producing compounds useful as Rho Kinase inhibitors and thus having utilities in the treatment of hypertension, atherosclerosis, restenosis, cerebral ischemia, cerebral vasospasm, neuronal degeneration, spinal cord injury, cancers of the breast, colon, prostate, ovaries, brain and lung and their metastases, thrombotic disorders, asthma, glaucoma and osteoporosis, as well as erectile dysfunction, i.e., erectile dysfunction mediated by Rho-kinase. Erectile dysfunction can be defined as an inability to obtain or sustain an erection adequate for intercourse, WO 94/28902, U.S. Pat. No. 6,103,765 and U.S. Pat. No. 6,124,461.

The invention pertains to a process for the preparation of a compound of Formula (I)

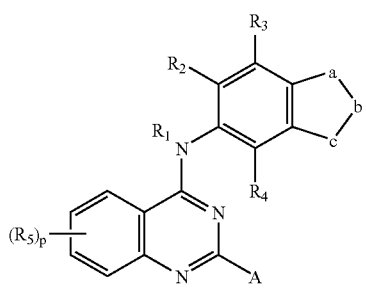
(I)

comprising reacting a compound of Formula 1

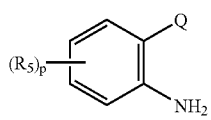
1 with a compound of Formula

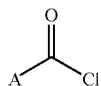

to produce a compound of Formula 2

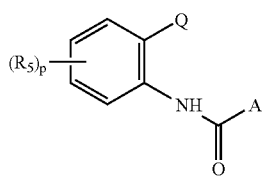
2 cyclizing 2 to form a compound of Formula 3

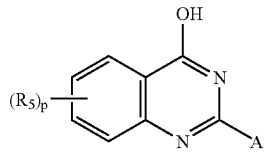
3 replacing the hydroxy group of 3 with a leaving group LG to form a compound of Formula 4

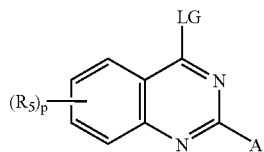
4 optionally isolating said compound of Formula 4;

reacting a mixture of said compound of Formula 4 and a compound of Formula 5

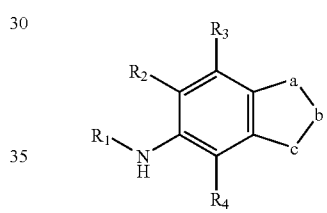
5 and optionally isolating said compound of Formula (I);

wherein in Formulae 3, 4, 5 and (I)

a and c are each independently —$CR_5$=, —N=, or —$NR_6$—, wherein one of a or c is —$NR_6$—;

b is —$CR_5$= or —N=;

A is a 3-20 atom, cyclic or polycyclic moiety, e.g., containing 1-4 rings, which optionally contain 1-3 N, O or S atoms per ring, and may optionally be aryl or heteroaryl, which cyclic or polycyclic moiety may optionally be substituted up to 3 times by (i)$C_1$-$C_{10}$ alkyl or $C_2$-$C_{10}$-alkenyl, each optionally substituted with halogen up to perhalo; (ii) $C_3$-$C_{10}$ cycloalkyl; (iii) aryl; (iv) heteroaryl; (v) halogen; (vi) —CO—$OR_8$; (vii) —CO—$R_8$; (viii) cyano; (ix) —$OR_8$, (x) —$NR_8R_{13}$; (xi) nitro; (xii) —CO—$NR_8R_9$; (xiii) —$C_{1-10}$-alkyl-$NR_8R_9$; (xiv) —$NR_8$—CO—$R_{12}$; (xv) —$NR_8$—CO—$OR_9$; (xvi) —$NR_8$—$SO_2$—$R_9$; (xvii) —$SR_8$; (xviii) —$SO_2$—$R_8$; (xix) —$SO_2$—$NR_8R_9$; or (xx) $NR_8$—CO—$NHR_9$;

$R_1$, $R_6$ and $R_8$—$R_{11}$ are each independently H or $C_{1-6}$ alkyl;

$R_2$-$R_5$ are each independently (i) $C_{1-10}$ alkyl or $C_{2-10}$-alkenyl each optionally substituted by amino, N-lower alkylamino, N,N-dilower alkylamino, N-lower alkanoylamino, hydroxy, cyano, —$COOR_{10}$, —$COR_{14}$, —$OCOR_{14}$, —$OR_{10}$, $C_{5-10}$-heteroaryl, $C_{5-10}$-heteroaryloxy, or $C_{5-10}$-heteroaryl-$C_{1-10}$-alkoxy, halogen up to perhalo; (ii) $C_3$-$C_{10}$ cycloalkyl, in which 1-3 carbon atoms are optionally independently replaced by O, N or S; (iii) $C_{3-10}$-cycloalkenyl; (iv) partially unsaturated $C_{5-10}$-heterocyclyl; (v) aryl; (vi) heteroaryl; (vii) halogen; (viii) —CO—OR$_{10}$; (ix) —OCOR$_{10}$; (x) —OCO$_2$R$_{10}$; (xi) —CHO; (xii) cyano; (xiii) —OR$_{16}$; (xiv) —NR$_{10}$R$_{15}$; (xv) nitro; (xvi) —CO—NR$_{10}$R$_{11}$; (xvii) —NR$_{10}$—CO—R$_{12}$; (xviii) —NR$_{10}$—CO—OR$_{11}$; (xix) —NR$_{10}$—SO$_2$—R$_{12}$; (xx) —SR$_{16}$; (xxi) —SOR$_{16}$; (xxii) —SO$_2$—R$_{16}$; (xxiii) —SO$_2$—NR$_{10}$R$_{11}$; (xxiv) NR$_{10}$—CO—NHR$_{11}$; (xxv) amidino; (xxvi) guanidino; (xxvii) sulfo; (xxviii) —B(OH)$_2$; (xxix) —OCON(R$_{10}$)$_2$; or (xxx) —NR$_{10}$CON(R$_{10}$)$_2$;

R$_{12}$ is H, $C_{1-6}$-alkyl or $C_{5-10}$-aryl,

R$_{13}$ is H, $C_{1-6}$-alkyl or $C_{1-6}$-alkoxy,

R$_{14}$ is lower alkyl or phenyl;

R$_{15}$ is lower alkyl, halogen, amino, N-lower alkyl amino, N,N-dilower alkylamino, N-lower alkanoylamino, OH, CN, COOR$_{10}$, —COR$_{14}$ or —OCOR$_{14}$;

R$_{16}$ is hydrogen, $C_{1-6}$-alkyl optionally substituted by halogen, up to perhalo, or $C_{5-10}$-heteroaryl;

p=0, 1, 2 or 3;

LG is Br or S-alkyl; and

Q is CONH$_2$;

with the proviso that A is not phenyl.

Moreover, the invention pertains to a process for the preparation of a compound of Formula (I)

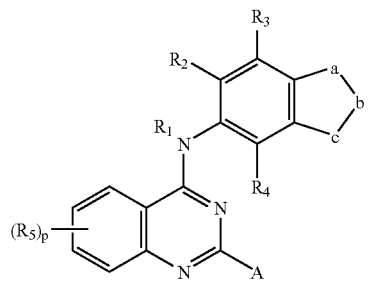

(I)

comprising reacting a compound of Formula 4

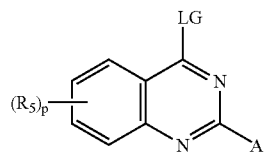

4 and a compound of Formula 5

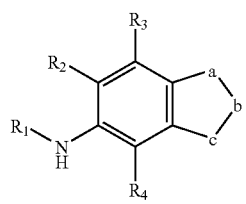

5 wherein in Formulas 3, 4, 5 and (I)

a and c are each independently —CR$_5$═, —N═, or —NR$_6$—, wherein one of a or c is —NR$_6$—;

b is —CR$_5$═ or —N═;

A is a 3-20 atom, cyclic or polycyclic moiety, e.g., containing 1-4 rings, which optionally contain 1-3 N, O or S atoms per ring, and may optionally be aryl or heteroaryl, which cyclic or polycyclic moiety may optionally be substituted up to 3 times by (i) $C_1$-$C_{10}$ alkyl or $C_2$-$C_{10}$-alkenyl, each optionally substituted with halogen up to perhalo; (ii) $C_3$-$C_{10}$ cycloalkyl; (iii) aryl; (iv) heteroaryl; (v) halogen; (vi) —CO—OR$_8$; (vii) —CO—R$_8$; (viii) cyano; (ix) —OR$_8$, (x) —NR$_8$R$_{13}$; (xi) nitro; (xii) —CO—NR$_8$R$_9$; (xiii) —C$_{1-10}$-alkyl-NR$_8$R$_9$; (xiv) —NR$_8$—CO—R$_{12}$; (xv) —NR$_8$—CO—OR$_9$; (xvi) —NR$_8$—SO$_2$—R$_9$; (xvii) —SR$_8$; (xviii) —SO$_2$—R$_8$; (xix) —SO$_2$—NR$_8$R$_9$; or (xx) NR$_8$—CO—NHR$_9$;

R$_1$, R$_6$ and R$_8$-R$_{11}$ are each independently H or $C_{1-6}$ alkyl;

R$_2$-R$_5$ are each independently (i) $C_{1-10}$ alkyl or $C_{2-10}$-alkenyl each optionally substituted by amino, N-lower alkylamino, N,N-dilower alkylamino, N-lower alkanoylamino, hydroxy, cyano, —COOR$_{10}$, —COR$_{14}$, —OCOR$_{14}$, —OR$_{10}$, $C_{5-10}$-heteroaryl, $C_{5-10}$-heteroaryloxy, or $C_{5-10}$-heteroaryl-$C_{1-10}$-alkoxy, halogen up to perhalo; (ii) $C_3$-$C_{10}$ cycloalkyl, in which 1-3 carbon atoms are optionally independently replaced by O, N or S; (iii) $C_{3-10}$-cycloalkenyl; (iv) partially unsaturated $C_{5-10}$-heterocyclyl; (v) aryl; (vi) heteroaryl; (vii) halogen; (viii) —CO—OR$_{10}$; (ix) —OCOR$_{10}$; (x) —OCO$_2$R$_{10}$;(xi) —CHO; (xii) cyano; (xiii) —OR$_{16}$; (xiv) —NR$_{10}$R$_{15}$; (xv) nitro; (xvi) —CO—NR$_{10}$R$_{11}$; (xvii) —NR$_{10}$—CO—R$_{12}$; (xviii) —NR$_{10}$—CO—OR$_{11}$; (xix) —NR$_{10}$—SO$_2$—R$_{12}$; (xx) —SR$_{16}$; (xxi) —SOR$_{16}$; (xxii) —SO$_2$—R$_{16}$; (xxiii) —SO$_2$—NR$_{10}$R$_{11}$; (xxiv) NR$_{10}$—CO—NHR$_{11}$; (xxv) amidino; (xxvi) guanidino; (xxvii) sulfo; (xxviii) —B(OH)$_2$; (xxix) —OCON(R$_{10}$)$_2$; or (xxx) —NR$_{10}$CON(R$_{10}$)$_2$;

R$_{12}$ is H, $C_{1-6}$-alkyl or $C_{5-10}$-aryl,

R$_{13}$ is H, $C_{1-6}$-alkyl or $C_{1-6}$-alkoxy,

R$_{14}$ is lower alkyl or phenyl;

R$_{15}$ is lower alkyl, halogen, amino, N-lower alkyl amino, N,N-dilower alkylamino, N-lower alkanoylamino, OH, CN, COOR$_{10}$, —COR$_{14}$ or —OCOR$_{14}$;

R$_{16}$ is hydrogen, $C_{1-6}$-alkyl optionally substituted by halogen, up to perhalo, or $C_{5-10}$-heteroaryl;

p=0,1,2 or 3; and

LG is Br or S-alkyl;

with the proviso that A is not phenyl.

The invention also pertains to a process for the preparation of a compound of Formula 3

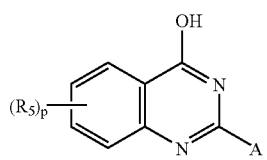

3 from a compound of Formula 2

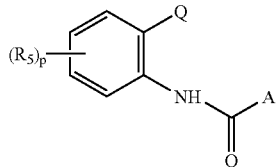

comprising mixing said compound of Formula 2, where Q is —CO—NH$_2$, with about 0.1 N to about 10 N aqueous hydroxide, and heating from a temperature of about 30° C. to about 120° C.;

wherein

A is a 3-20 atom, cyclic or polycyclic moiety, e.g., containing 1-4 rings, which optionally contain 1-3 N, O or S atoms per ring, and may optionally be aryl or heteroaryl, which cyclic or polycyclic moiety may optionally be substituted up to 3 times by (i) C$_1$-C$_{10}$ alkyl or C$_2$-C$_{10}$-alkenyl, each optionally substituted with halogen up to perhalo; (ii) C$_3$-C$_{10}$ cycloalkyl; (iii) aryl; (iv) heteroaryl; (v) halogen; (vi) —CO—OR$_8$; (vii) —CO—R$_8$; (viii) cyano; (ix) —OR$_8$, (x) —NR$_8$R$_{13}$; (xi) nitro; (xii) —CO—NR$_8$R$_9$; (xiii) —C$_{1-10}$-alkyl-NR$_8$R$_9$; (xiv) —NR$_8$—CR$_{12}$; (xv) —NR$_8$—CO—OR$_9$; (xvi) —NR$_8$—SO$_2$—R$_9$; (xvii) —SR$_8$; (xviii) —SO$_2$—R$_8$; (xix) —SO$_2$—NR$_8$R$_9$; or (xx) NR$_8$—CO—NHR$_9$;

R$_5$ is (i) C$_{1-10}$ alkyl or C$_{2-10}$-alkenyl each optionally substituted by amino, N-lower alkylamino, N,N-dilower alkylamino, N-lower alkanoylamino, hydroxy, cyano, —COOR$_{10}$, —COR$_{14}$, —OCOR$_{14}$, —OR$_{10}$, C$_{5-10}$-heteroaryl, C$_{5-10}$-heteroaryloxy, or C$_{5-10}$-heteroaryl-C$_{1-10}$-alkoxy, halogen up to perhalo; (ii) C$_3$-C$_{10}$ cycloalkyl, in which 1-3 carbon atoms are optionally independently replaced by O, N or S; (iii) C$_{3-10}$-cycloalkenyl; (iv) partially unsaturated C$_{5-10}$-heterocyclyl; (v) aryl; (vi) heteroaryl; (vii) halogen; (viii) —CO—OR$_{10}$; (ix) —OCOR$_{10}$; (x) —OCO$_2$R$_{10}$; (xi) —CHO; (xii) cyano; (xiii) —OR$_{16}$; (xiv) —NR$_{10}$R$_{15}$; (xv) nitro; (xvi) —CO—NR$_{10}$R$_{11}$; (xvii) —NR$_{10}$—CO—R$_{12}$; (xviii) —NR$_{10}$—CO—OR$_{11}$; (xix) —NR$_{10}$—SO$_2$—R$_{12}$; (xx) —SR$_{16}$; (xxi) —SOR$_{16}$; (xxii) —SO$_2$—R$_{16}$; (xxiii) —SO$_2$—NR$_{10}$R$_{11}$; (xxiv) NR$_{10}$—CO—NHR$_{11}$; (xxv) amidino; (xxvi) guanidino; (xxvii) sulfo; (xxviii) —B(OH)$_2$; (xxix) —OCON(R$_{10}$)$_2$; or (xxx) —NR$_{10}$CON(R$_{10}$)$_2$;

p=0,1,2, or 3

R$_8$-R$_{11}$ are each independently H or C$_{1-6}$ alkyl

R$_{12}$ is H, C$_{1-6}$-alkyl or C$_{5-10}$-aryl,

R$_{13}$ is H, C$_{1-6}$-alkyl or C$_{1-6}$-alkoxy,

R$_{14}$ is lower alkyl or phenyl;

R$_{15}$ is lower alkyl, halogen, amino, N-lower alkyl amino, N,N-dilower alkylamino, N-lower alkanoylamino, OH, CN, COOR$_{10}$, —COR$_{14}$ or —OCOR$_{14}$;

R$_{16}$ is hydrogen, C$_{1-6}$-alkyl optionally substituted by halogen, up to perhalo, or C$_{5-10}$-heteroaryl, and wherein Formulas 2 and 3 encompass tautomers, optical isomers, or salts thereof.

The invention also pertains to a process for the preparation of a compound of Formula 3,

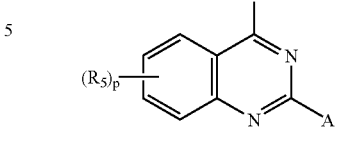

from a carboxylic acid of Formula A-CO$_2$H and a compound of Formula 1,

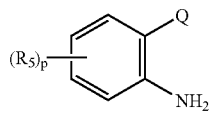

comprising, in a single vessel, treating said carboxylic acid with a chlorinating agent, with optional addition of a catalytic amount of DMF, to form an acid chloride of Formula A-CO—Cl;

adding a non-nucleophilic amine base and a non-protic solvent with stirring at room temperature to form a compound of Formula 2;

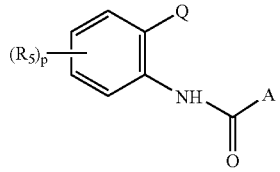

and adding of a base and heating the mixture up to about 50° C.; for a sufficient time to effect reaction;

wherein Q is CO—NH$_2$,

A is a 3-20 atom, cyclic or polycyclic moiety, e.g., containing 1-4 rings, which optionally contain 1-3 N, O or S atoms per ring, and may optionally be aryl or heteroaryl, which cyclic or polycyclic moiety may optionally be substituted up to 3 times by (i) C$_1$-C$_{10}$ alkyl or C$_2$-C$_{10}$-alkenyl, each optionally substituted with halogen up to perhalo; (ii) C$_3$-C$_{10}$ cycloalkyl; (iii) aryl; (iv) heteroaryl; (v) halogen; (vi) —CO—OR$_8$; (vii) —CO—R$_8$; (viii) cyano; (ix) —OR$_8$, (x) —NR$_8$R$_{13}$; (xi) nitro; (xii) —CO—NR$_8$R$_9$; (xiii) —C$_{1-10}$-alkyl-NR$_8$R$_9$; (xiv) —NR$_8$—CO—R$_{12}$; (xv) —NR$_8$—CO—OR$_9$; (xvi) —NR$_8$—SO$_2$—R$_9$; (xvii) —SR$_8$; (xviii) —SO$_2$—R$_8$; (xix) —SO$_2$—NR$_8$R$_9$; or (xx) NR$_8$—CO—NHR$_9$;

R$_5$ is (i) C$_{1-10}$ alkyl or C$_{2-10}$-alkenyl each optionally substituted by amino, N-lower alkylamino, N,N-dilower alkylamino, N-lower alkanoylamino, hydroxy, cyano, —COOR$_{10}$, —COR$_{14}$, —OCOR$_{14}$, —OR$_{10}$, C$_{5-10}$-heteroaryl, C$_{5-10}$-heteroaryloxy, or C$_{5-10}$-heteroaryl-C$_{1-10}$-alkoxy, halogen up to perhalo; (ii) C$_3$-C$_{10}$ cycloalkyl, in which 1-3 carbon atoms are optionally independently replaced by O, N or S; (iii) C$_{3-10}$-cycloalkenyl; (iv) partially unsaturated $C_{5-10}$-heterocyclyl; (v) aryl; (vi) heteroaryl; (vii) halogen; (viii) —CO—OR$_{10}$; (ix) —OCOR$_{10}$; (x) —OCO$_2$R$_{10}$; (xi) —CHO; (xii) cyano; (xiii) —OR$_{16}$; (xiv) —NR$_{10}$R$_{15}$; (xv) nitro; (xvi) —CO—NR$_{10}$R$_{11}$; (xvii) —NR$_{10}$—CO—R$_{12}$; (xviii) —NR$_{10}$—CO—OR$_{11}$; (xix) —NR$_{10}$—SO$_2$—R$_{12}$; (xx) —SR$_{16}$; (xxi) —SOR$_{16}$; (xxii) —SO$_2$—R$_{16}$; (xxiii) —SO$_2$—NR$_{10}$R$_{11}$; (xxiv) NR$_{10}$—CO—NHR$_{11}$; (xxv) amidino; (xxvi) guanidino; (xxvii) sulfo; (xxviii) —B(OH)$_2$; (xxix) —OCON(R$_{10}$)$_2$; or (xxx) —NR$_{10}$CON(R$_{10}$)$_2$;

p=0, 1, 2, or 3

$R_8$-$R_{11}$ are each independently H or $C_{1-6}$ alkyl $R_{12}$ is H, $C_{1-6}$-alkyl or $C_{5-10}$-aryl, $R_{13}$ is H, $C_{1-6}$-alkyl or $C_{1-6}$-alkoxy, $R_{14}$ is lower alkyl or phenyl;

$R_{15}$ is lower alkyl, halogen, amino, N-lower alkyl amino, N,N-dilower alkylamino, N-lower alkanoylamino, OH, CN, COOR$_{10}$, —COR$_{14}$ or —OCOR$_{14}$; $R_{16}$ is hydrogen, $C_{1-6}$-alkyl optionally substituted by halogen, up to perhalo, or $C_{5-10}$-heteroaryl, and wherein Formulas 2 and 3 encompass tautomers, optical isomers, or salts thereof.

The invention also pertains to a process for the preparation of a compound of Formula (I)

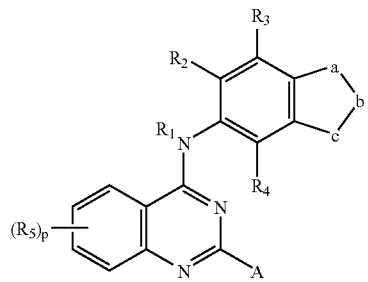

(I)

comprising replacing the hydroxy group of a compound of Formula 3

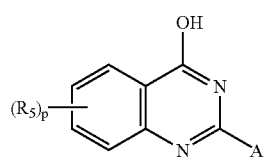

3 with a leaving group LG to form a compound of Formula 4

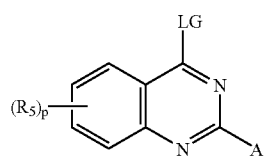

4 optionally isolating said compound of Formula 4;

reacting a mixture of said compound of Formula 4 and a compound of Formula 5

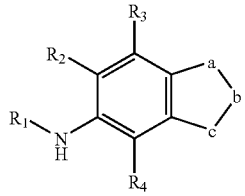

5 and optionally isolating said compound of Formula (I);

wherein in Formulae 3, 4, 5 and (I)

a and c are each independently —CR$_5$=, —N=, or —NR$_6$—, wherein one of a or c is —NR$_6$—;

b is —CR$_5$= or —N=;

A is a 3-20 atom, cyclic or polycyclic moiety, e.g., containing 1-4 rings, which optionally contain 1-3 N, O or S atoms per ring, and may optionally be aryl or heteroaryl, which cyclic or polycyclic moiety may optionally be substituted up to 3 times by (i) $C_1$-$C_{10}$ alkyl or $C_2$-$C_{10}$-alkenyl, each optionally substituted with halogen up to perhalo; (ii) $C_3$-$C_{10}$ cycloalkyl; (iii) aryl; (iv) heteroaryl; (v) halogen; (vi) —CO—OR$_8$; (vii) —CO—R$_8$; (viii) cyano; (ix) —OR$_8$, (x) —NR$_8$R$_{13}$; (xi) nitro; (xii) —CO—NR$_8$R$_9$; (xiii) —$C_{1-10}$-alkyl-NR$_8$R$_9$; (xiv) —NR$_8$—CO—R$_{12}$; (xv) —NR$_8$—CO—OR$_9$; (xvi) —NR$_8$—SO$_2$—R$_9$; (xvii) —SR$_8$; (xviii) —SO$_2$—R$_8$; (xix) —SO$_2$—NR$_8$R$_9$; or (xx) NR$_8$—CO—NHR$_9$;

$R_1$, $R_6$ and $R_8$—$R_{11}$ are each independently H or $C_{1-6}$ alkyl;

$R_2$-$R_5$ are each independently (i) $C_{1-10}$ alkyl or $C_{2-10}$-alkenyl each optionally substituted by amino, N-lower alkylamino, N,N-dilower alkylamino, N-lower alkanoylamino, hydroxy, cyano, —COOR$_{10}$, —COR$_{14}$, —OCOR$_{14}$, —OR$_{10}$, $C_{5-10}$-heteroaryl, $C_{5-10}$-heteroaryloxy, or $C_{5-10}$-heteroaryl-$C_{1-10}$-alkoxy, halogen up to perhalo; (ii) $C_3$-$C_{10}$ cycloalkyl, in which 1-3 carbon atoms are optionally independently replaced by O, N or S; (iii) $C_{3-10}$-cycloalkenyl; (iv) partially unsaturated $C_{5-10}$-heterocyclyl; (v) aryl; (vi) heteroaryl; (vii) halogen; (viii) —CO—OR$_{10}$; (ix) —OCOR$_{10}$; (x) —OCO$_2$R$_{10}$; (xi) —CHO; (xii) cyano; (xiii) —OR$_{16}$; (xiv) —NR$_{10}$R$_{15}$; (xv) nitro; (xvi) —CO—NR$_{10}$R$_{11}$; (xvii) —NR$_{10}$—CO—R$_{12}$; (xviii) —NR$_{10}$—CO—OR$_{11}$; (xix) —NR$_{10}$—SO$_2$-R$_{12}$; (xx) —SR$_{16}$; (xxi) —SOR$_{16}$; (xxii) —SO$_2$—R$_{16}$; (xxiii) —SO$_2$—NR$_{10}$R$_{11}$; (xxiv) NR$_{10}$—CO—NHR$_{11}$; (xxv) amidino; (xxvi) guanidino; (xxvii) sulfo; (xxviii) —B(OH)$_2$; (xxix) —OCON(R$_{10}$)$_2$; or (xxx) —NR$_{10}$CON(R$_{10}$)$_2$;

$R_{12}$ is H, $C_{1-6}$-alkyl or $C_{5-10}$-aryl, $R_{13}$ is H, $C_{1-6}$-alkyl or $C_{1-6}$-alkoxy, $R_{14}$ is lower alkyl or phenyl;

$R_{15}$ is lower alkyl, halogen, amino, N-lower alkyl amino, N,N-dilower alkylamino, N-lower alkanoylamino, OH, CN, COOR$_{10}$, —COR$_{14}$ or —OCOR$_{14}$;

$R_{16}$ is hydrogen, $C_{1-6}$-alkyl optionally substituted by halogen, up to perhalo, or $C_{5-10}$-heteroaryl;

p=0,1,2 or 3; and

LG is Br or S-alkyl with the proviso that A is not phenyl.

The invention also pertains to a process for the preparation of a compound of Formula (I)

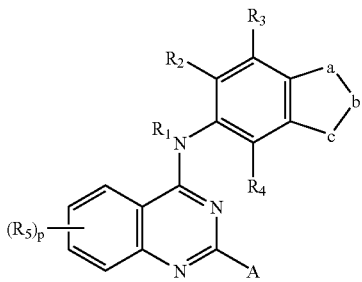

comprising reacting a compound of Formula 1

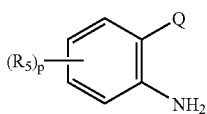

with a compound of Formula

to produce a compound of Formula 2

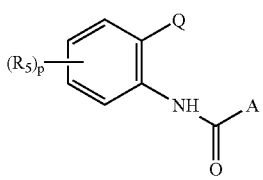

cyclizing 2 to form a compound of Formula 3

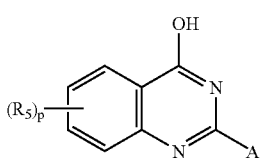

replacing the hydroxy group of 3 with a leaving group to form a compound of Formula 4'

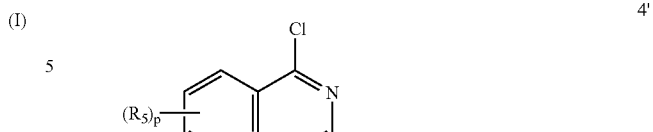

optionally isolating said compound of Formula 4';

reacting a mixture of said compound of Formula 4' and a compound of Formula 5

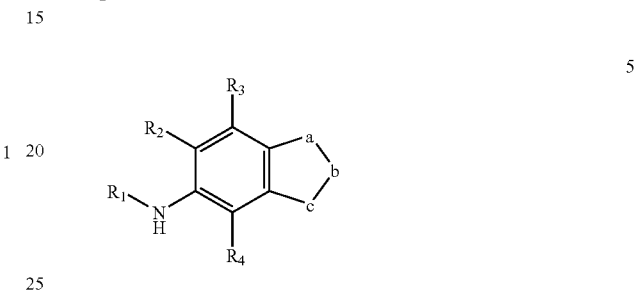

wherein in Formulas 3, 4', 5 and (I)

a and c are each independently —$CR_5$=, —N=, or —$NR_6$—, wherein one of a or c is —$NR_6$—;

b is —$CR_5$= or —N=;

A is a 3-20 atom, cyclic or polycyclic moiety, e.g., containing 1-4 rings, which optionally contain 1-3 N, O or S atoms per ring, and may optionally be aryl or heteroaryl, which cyclic or polycyclic moiety may optionally be substituted up to 3 times by (i) $C_1$-$C_{10}$ alkyl or $C_2$-$C_{10}$-alkenyl, each optionally substituted with halogen up to perhalo; (ii) $C_3$-$C_{10}$ cycloalkyl; (iii) aryl; (iv) heteroaryl; (v) halogen; (vi) —CO—$OR_8$; (vii) —CO—$R_8$; (viii) cyano; (ix) —$OR_8$, (x) —$NR_8R_{13}$; (xi) nitro; (xii) —CO—$NR_8R_9$; (xiii) —$C_{1-10}$-alkyl-$NR_8R_9$; (xiv) —$NR_8$—CO—$R_{12}$; (xv) —$NR_8$—CO—$OR_9$; (xvi) —$NR_8$—$SO_2$—$R_9$; (xvii) —$SR_8$; (xviii) —$SO_2$—$R_8$; (xix) —$SO_2$—$NR_8R_9$; or (xx) $NR_8$—CO—$NHR_9$;

$R_1$, $R_6$ and $R_8$-$R_{11}$ are each independently H or $C_{1-6}$ alkyl;

$R_2$-$R_5$ are each independently (i) $C_{1-10}$ alkyl or $C_{2-10}$-alkenyl each optionally substituted by amino, N-lower alkylamino, N,N-dilower alkylamino, N-lower alkanoylamino, hydroxy, cyano, —$COOR_{10}$, —$COR_{14}$, —$OCOR_{14}$, —$OR_{10}$, $C_{5-10}$-heteroaryl, $C_{5-10}$-heteroaryloxy, or $C_{5-10}$-heteroaryl-$C_{1-10}$-alkoxy, halogen up to perhalo; (ii) $C_3$-$C_{10}$ cycloalkyl, in which 1-3 carbon atoms are optionally independently replaced by O, N or S; (iii) $C_{3-10}$-cycloalkenyl; (iv) partially unsaturated $C_{5-10}$-heterocyclyl; (v) aryl; (vi) heteroaryl; (vii) halogen; (viii) —CO—$OR_{10}$; (ix) —$OCOR_{10}$; (x) —$OCO_2R_{10}$; (xi) —CHO; (xii) cyano; (xiii) —$OR_{16}$; (xiv) —$NR_{10}R_{15}$; (xv) nitro; (xvi) —CO—$NR_{10}R_{11}$; (xvii) —$NR_{10}$—CO—$R_{12}$; (xviii) —$NR_{10}$—CO—$OR_{11}$; (xix) —$NR_{10}$—$SO_2$—$R_{12}$; (xx) —$SR_{16}$; (xxi) —$SOR_{16}$; (xxii) —$SO_2$—$R_{16}$; (xxiii) —$SO_2$—$NR_{10}R_{11}$; (xxiv) $NR_{10}$—CO—$NHR_{11}$; (xxv) amidino; (xxvi) guanidino; (xxvii) sulfo;(xxviii) —$B(OH)_2$; (xxix) —$OCON(R_{10})_2$; or (xxx) —$NR_{10}CON(R_{10})_2$;

$R_{12}$ is H, $C_{1-6}$-alkyl or $C_{5-10}$-aryl, $R_{13}$ is H, $C_{1-6}$-alkyl or $C_{1-6}$-alkoxy, $R_{14}$ is lower alkyl or phenyl;

$R_{15}$ is lower alkyl, halogen, amino, N-lower alkyl amino, N,N-dilower alkylamino, N-lower alkanoylamino, OH, CN, $COOR_{10}$, $—COR_{14}$ or $—OCOR_{14}$;

$R_{16}$ is hydrogen, $C_{1-6}$-alkyl optionally substituted by halogen, up to perhalo, or $C_{5-10}$-heteroaryl; and p=0,1,2 or 3;

LG is Cl, and

Q is CN, with the proviso that compound I is not

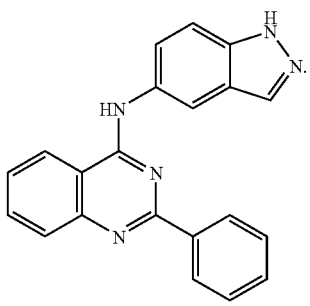

The invention also pertains to a process for the preparation of a compound of Formula (I)

(I)

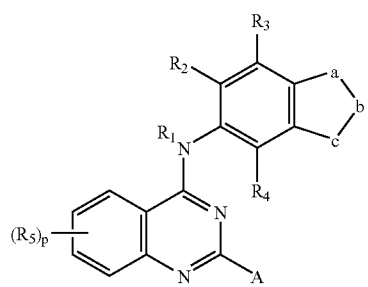

comprising reacting a compound of Formula 4'

4'

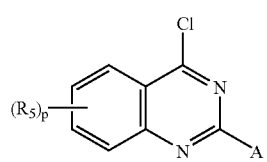

and a compound of Formula 5

5

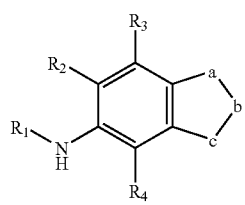

wherein in Formulas 3, 4', 5 and (I)

a and c are each independently $—CR_5=$, $—N=$, or $—NR_6—$, wherein one of a or c is $—NR_6—$;

b is $—CR_5=$ or $—N=$;

A is a 3-20 atom, cyclic or polycyclic moiety, e.g., containing 1-4 rings, which optionally contain 1-3 N, O or S atoms per ring, and may optionally be aryl or heteroaryl, which cyclic or polycyclic moiety may optionally be substituted up to 3 times by (i) $C_1$-$C_{10}$ alkyl or $C_2$-$C_{10}$-alkenyl, each optionally substituted with halogen up to perhalo; (ii) $C_3$-$C_{10}$ cycloalkyl; (iii) aryl; (iv) heteroaryl; (v) halogen; (vi) $—CO—OR_8$; (vii) $—CO—R_8$; (viii) cyano; (ix) $—OR_8$, (x) $—NR_8R_{13}$; (xi) nitro; (xii) $—CO—NR_8R_9$; (xiii) $—C_{1-10}$-alkyl-$NR_8R_9$; (xiv) $—NR_8—CO—R_{12}$; (xv) $—NR_8—CO—OR_9$; (xvi) $—NR_8—SO_2—R_9$; (xvii) $—SR_8$; (xviii) $—SO_2—R_8$; (xix) $—SO_2—NR_8R_9$; or (xx) $NR_8—CO—NHR_9$;

$R_1$, $R_6$ and $R_8$-$R_{11}$ are each independently H or $C_{1-6}$ alkyl;

$R_2$-$R_5$ are each independently (i) $C_{1-10}$ alkyl or $C_{2-10}$-alkenyl each optionally substituted by amino, N-lower alkylamino, N,N-dilower alkylamino, N-lower alkanoylamino, hydroxy, cyano, $—COOR_{10}$, $—COR_{14}$, $—OCOR_{14}$, $—OR_{10}$, $C_{5-10}$-heteroaryl, $C_{5-10}$-heteroaryloxy, or $C_{5-10}$-heteroaryl-$C_{1-10}$-alkoxy, halogen up to perhalo; (ii) $C_3$-$C_{10}$ cycloalkyl, in which 1-3 carbon atoms are optionally independently replaced by O, N or S; (iii) $C_{3-10}$-cycloalkenyl; (iv) partially unsaturated $C_{5-10}$-heterocyclyl; (v) aryl; (vi) heteroaryl; (vii) halogen; (viii) $—CO—OR_{10}$; (ix) $—OCOR_{10}$; (x) $—OCO_2R_{10}$; (xi) $—CHO$; (xii) cyano; (xiii) $—OR_{16}$; (xiv) $—NR_{10}R_{15}$; (xv) nitro; (xvi) $—CO—NR_{10}R_{11}$; (xvii) $—NR_{10}—CO—R_{12}$; (xviii) $—NR_{10}—CO—OR_{11}$; (xix) $—NR_{10}—SO_2—R_{12}$; (xx) $—SR_{16}$; (xxi) $—SOR_{16}$; (xxii) $—SO_2—R_{16}$; (xxiii) $—SO_2—NR_{10}R_{11}$; (xxiv) $NR_{10}—CO—NHR_{11}$; (xxv) amidino; (xxvi) guanidino; (xxvii) sulfo; (xxviii) $—B(OH)_2$; (xxix) $—OCON(R_{10})_2$; or (xxx) $—NR_{10}CON(R_{10})_2$;

$R_{12}$ is H, $C_{1-6}$-alkyl or $C_{5-10}$-aryl, $R_{13}$ is H, $C_{1-6}$-alkyl or $C_{1-6}$-alkoxy, $R_{14}$ is lower alkyl or phenyl;

$R_{15}$ is lower alkyl, halogen, amino, N-lower alkyl amino, N,N-dilower alkylamino, N-lower alkanoylamino, OH, CN, $COOR_{10}$, $—COR_{14}$ or $—OCOR_{14}$;

$R_{16}$ is hydrogen, $C_{1-6}$-alkyl optionally substituted by halogen, up to perhalo, or $C_{5-10}$-heteroaryl; and p=0,1,2 or 3;

with the proviso that compound I is not

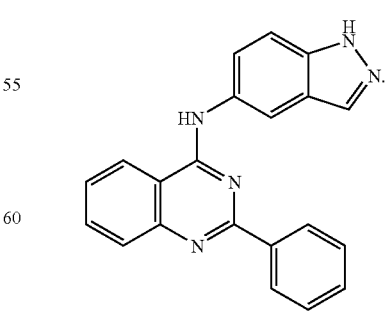

The invention also pertains to a process for the preparation of a compound of Formula I'

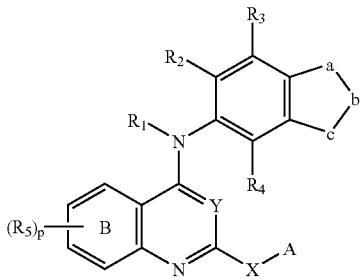

(I')

wherein Y is =N— or =CR$_{17}$,

X is —(CH$_2$)$_x$—, —O—(CH$_2$)$_n$—, —S—(CH$_2$)$_n$—, —NR$_7$—CO—(CH$_2$)$_n$—, —NR$_7$—SO$_2$—(CH$_2$)$_n$—, —NR$_7$—(CH$_2$)$_n$—, or —(O)C—NR$_7$—, each n is an integer which is independently 0, 1, 2 or 3, x is 0-3 p is 0-3 a and c are each independently —CR5=, —N=, or —NR6—, wherein one of a or c is —NR6—, and b is —CR5= or —N=;

A is H, halogen, —CO—OR$_8$, —CO—R$_8$, cyano, —OR$_8$, —NR$_8$R$_9$, —CO—NR$_8$R$_9$, —NR$_8$—CO—R$_9$, —NR$_8$—CO—OR$_9$, —NR$_8$—SO$_2$—R$_9$, —SR$_8$, —SO$_2$—R$_8$, —SO$_2$—NR$_8$R$_9$, NR$_8$—CO—NHR$_9$, or A is a 3-20 atom, cyclic or polycyclic moiety, containing 1-4 rings, which optionally contain 1-3 N, O or S atoms per ring, and may optionally be aryl or heteroaryl, which cyclic or polycyclic moiety may optionally be substituted up to 3 times by (i) C$_1$-C$_{10}$ alkyl or C$_2$-C$_{10}$-alkenyl, each optionally substituted with halogen up to perhalo; (ii) C$_3$-C$_{10}$ cycloalkyl; (iii) aryl; (iv) heteroaryl; (v) halogen; (vi) —CO—OR$_8$; (vii) —CO—R$_8$; (viii) cyano; (ix) —OR$_8$; (x)(x) —NR$_8$R$_{13}$; (xi) nitro; (xii) —CO—NR$_8$R$_9$; (xiii) —C$_{1-10}$-alkyl-NR$_8$R$_9$; (xiv) —NR$_8$—CO—R$_{12}$; (xv) —NR$_8$CO—OR$_9$; (xvi) —NR$_8$—SO$_2$—R$_9$; (xvii) —SR$_8$; (xviii) —SO$_2$—R$_8$; (xix) —SO$_2$—NR$_8$R$_9$; or (xx) NR$_8$—CO—NHR$_9$;

Ring B is optionally independently substituted up to 3 times in any position by R$_5$, R$_1$ and R$_{6-11}$ are each independently hydrogen or C$_{1-6}$alkyl, R$_2$-R$_5$ are each independently (i) hydrogen, (ii) C$_{1-10}$ alkyl or C$_{2-10}$-alkenyl each optionally substituted by amino, N-lower alkylamino, N,N-dilower alkylamino, N-lower alkanoylamino, hydroxy, cyano, —COOR$_{10}$, —COR$_{14}$, —OCOR$_{14}$, —OR$_{10}$, C$_{5-10}$-heteroaryl, C$_{5-10}$-heteroaryloxy, or C$_{5-10}$-heteroaryl-C$_{1-10}$-alkoxy, halogen up to perhalo; (iii) C$_{3-10}$ cycloalkyl, in which 1-3 carbon atoms are optionally independently replaced by O, N or S; (iv) C$_{3-10}$-cycloalkenyl; (v) partially unsaturated C$_{5-10}$-heterocyclyl; (vi) aryl; (vii) heteroaryl; (viii) halogen; (ix) —CO—OR$_{10}$; (x) —OCOR$_{10}$; (xi) —OCO$_2$R$_{10}$; (xii) —CHO; (xiii) cyano; (xiv) —OR$_{16}$; (xv) —NR$_{10}$R$_{15}$; (xvi) nitro; (xvii) —CO—NR$_{10}$R$_{11}$; (xviii) —NR$_{10}$—CO—R$_{12}$; (xix) —NR$_{10}$—CO—OR$_{11}$; (xx) —NR$_{10}$—SO$_2$R$_{12}$; (xxi) —SR$_{16}$; (xxii) —SOR$_{16}$; (xxiii) —SO$_2$—R$_{16}$; (xxiv) —SO$_2$—NR$_{10}$R$_{11}$; (xxv) NR$_{10}$—CO—NHR$_{11}$; (xxvi) amidino; (xxvii) guanidine; (xxviii) sulfo; (xxix) —B(OH)$_2$; (xxx) —OCON(R$_{10}$)$_2$; or (xxxi) —NR$_{10}$CON(R$_{10}$)$_2$;

R$_{12}$ is H, C$_{1-6}$-alkyl or C$_{5-10}$-aryl,

R$_{13}$ is H, C$_{1-6}$-alkyl or C$_{1-6}$-alkoxy,

R$_{14}$ is C$_{1-6}$ alkyl or phenyl;

R$_{15}$ is C$_{1-6}$ alkyl, halogen, amino, N-lower alkyl amino, N,N dilower alkylamino, N-lower alkanoylamino, OH, CN, COOR$_{10}$, —COR$_{14}$ or —OCOR$_{14}$;

R$_{16}$ is hydrogen, C$_{1-6}$-alkyl optionally substituted by halogen, up to perhalo, or C$_{5-10}$-heteroaryl; and R$_{17}$ is H, C$_{1-6}$ alkyl or CN, or a pharmaceutically acceptable salt thereof, with the provisos that A is not hydrogen when x is 0, and that Formula I is not

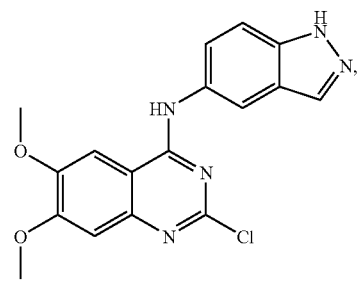

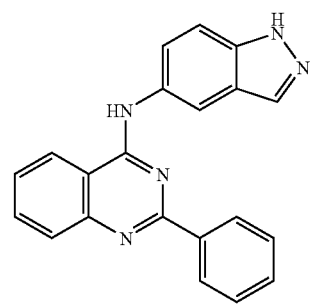

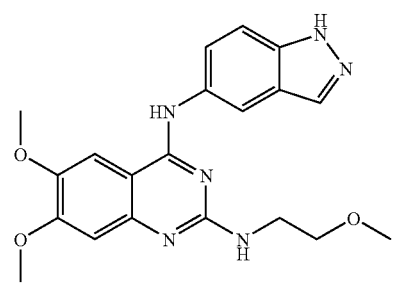

,

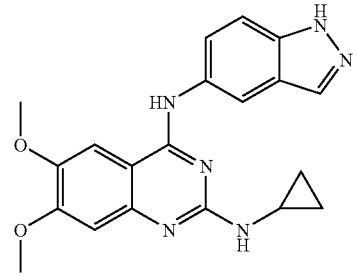

-continued

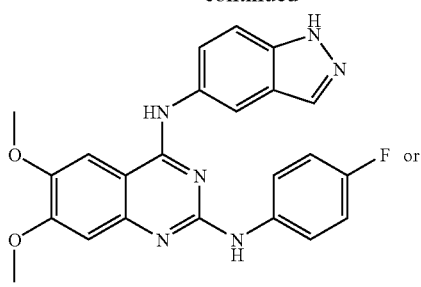

F or

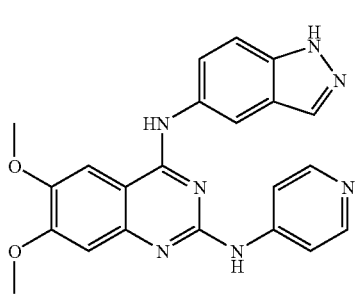

said process comprising (a) reacting a compound of Formula II

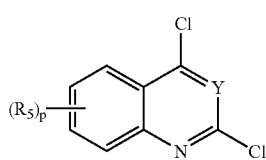
(II)

with a compound of Formula III

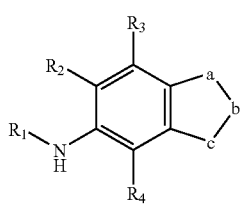
(III)

in the presence of a base, to produce a compound of Formula IV

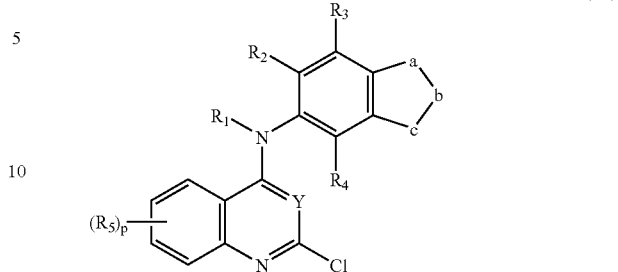
(IV)

and optionally further reacting IV with arylboronic acid or A-NH$_2$, or (b) reacting a substituted benzoyl chloride with dimethylamine to produce a compound of Formula V

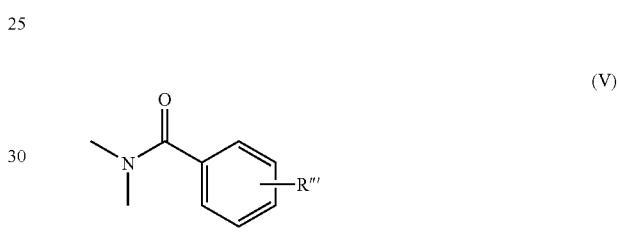
(V)

wherein R''' is (i) $C_1$-$C_{10}$ alkyl or $C_2$-$C_{10}$-alkenyl, each optionally substituted with halogen up to perhalo; (ii) $C_3$-$C_{10}$ cycloalkyl; (iii) aryl; (iv) heteroaryl; (v) halogen; (vi) —CO—OR$_8$; (vii) —CO—R$_8$; (viii) cyano; (ix) —OR$_8$, (x) (x) —NR$_8$R$_{13}$; (xi) nitro; (xii) —CO—NR$_8$R$_9$; (xiii) —C$_{1-10}$-alkyl-NR$_8$R$_9$; (xiv) —NR$_8$—CO—R$_{12}$; (xv) —NR$_8$—CO—OR$_9$; (xvi) —NR$_8$—SO$_2$—R$_9$; (xvii) —SR$_8$; (xviii) —SO$_2$—R$_8$; (xix) —SO$_2$—NR$_8$R$_9$; or (xx) NR$_8$—CO—NHR$_9$, reacting V with chloro-2-amino-benzonitrile to produce a compound of Formula VI

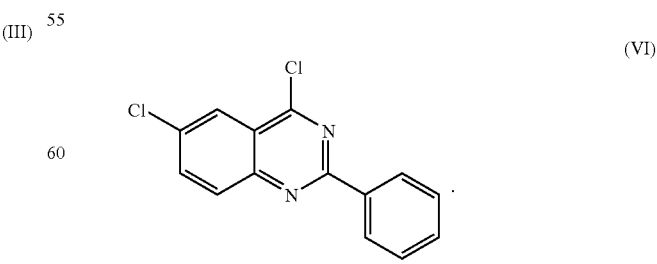
(VI)

and reacting VI with aminoindazole.

The invention also pertains to a process for preparing

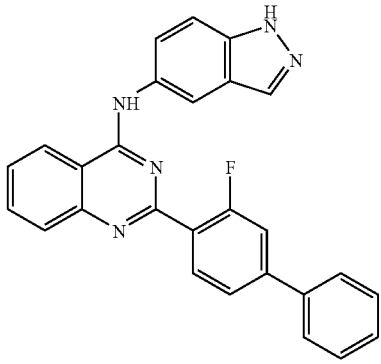

comprising reacting 3-fluoro-4-phenylbenzoic acid

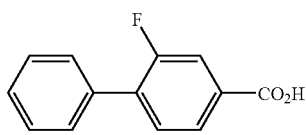

with 4-bromo-2-fluorobiphenyl to produce 2[(3-fluoro-4-phenylphenyl)carbonylamino]-benzamide

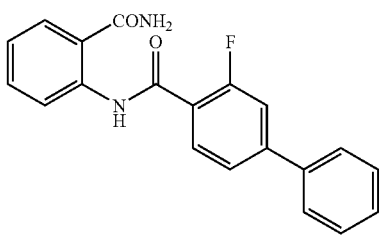

cyclizing to produce 2-(3-fluoro-1,1'-biphenyl-4-yl)-4(3H-quinazolinone

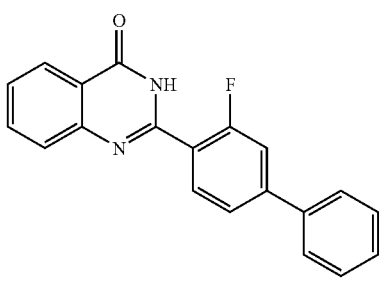

reacting to produce 4-chloro-2-(3-fluoro-4-phenylphenyl)quinazoline

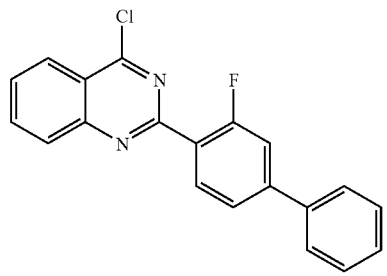

and then reacting with aminoindazole to produce

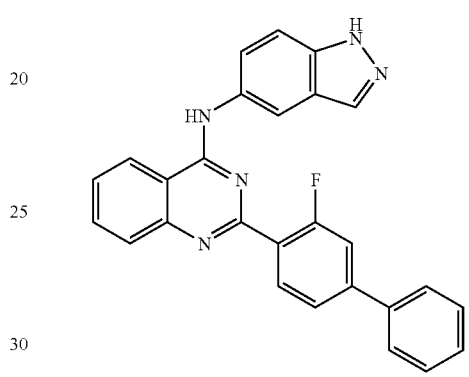

In particular, the invention also pertains to a method of preparation of a compound of Formula (I)

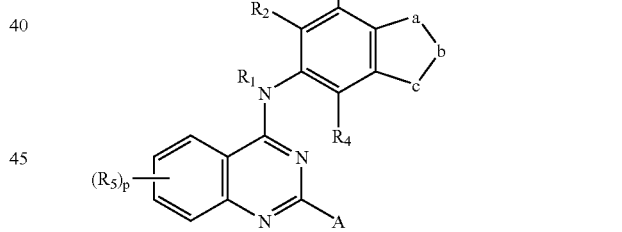

(I)

from the above described compounds of Formula 3 comprising the steps of
(1) heating of said Formula 3 compound with a chlorinating agent, (with the optional addition of DMF), to form a compound of Formula 4'

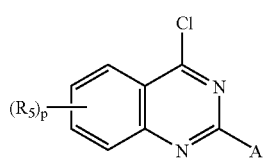

4'

(2) isolation of said compound of Formula 4';
(3) addition of a non-nucleophilic base to a mixture of said compound of Formula 4' and a compound of Formula 5

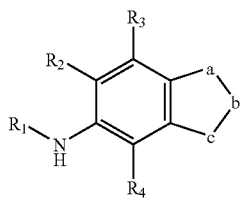

in a higher boiling solvent;
(4) heating said mixture at reflux (up from 5 to about 20 hours) for a time sufficient to effect reaction; and
(5) isolation of said compound of Formula (I).

Moreover, the present invention pertains to a method of preparation of a compound of Formula 3

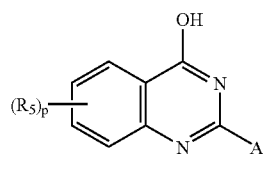

from a compound of Formula 2

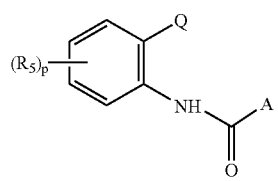

comprising the steps of
(1) (a) mixing said compound of Formula 2, where Q is —CO—NH$_2$, with about 0.1 N to about 10 N (or 20%) aqueous hydroxide,
or
(1) (b) mixing said compound of Formula 2, where Q is —CN,—with about 0.1 N to about 10 N (or 20%) aqueous hydroxide and about 3—to about 30% H$_2$O$_2$, or with about 0.5 to 2.5 M mineral acid,
(2) heating the mixture from a temperature of about 30° C. to about 120° C.

The invention also pertains to a method of preparation of a compound of Formula 3, from a carboxylic acid of Formula A-CO$_2$H and a compound of Formula 1,

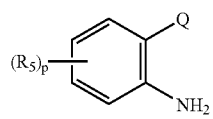

comprising the steps of
(1) treatment of the said carboxylic acid with a chlorinating agent, with the optional addition of a catalytic amount of DMF, to form an acid chloride of Formula A-CO—Cl;

(2) addition of a non-nucleophilic amine base and a non-protic solvent with stirring at room temperature to form the compound of Formula 2; and
(3) addition of a base and heating the mixture up to about 50° C. (for about 90 minutes); for a sufficient time to effect reaction;

wherein the steps are conducted in a single vessel;
and in Formulas 1, 2 and 3
Q is CO—NH$_2$;
and R$_5$, A, and p are as defined above;
and the tautomers, optical isomers and salts thereof.

A schematic representation of the methods of preparation encompassed by this invention is summarized in Reaction Scheme 1 below. In the structures depicted, A, R$_1$-R$_5$, a, b, c and p have the meanings described above.

Reaction Scheme 1

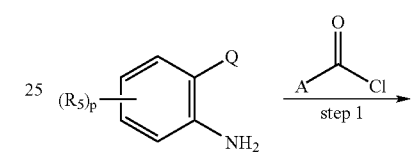

1

Q = CN or CONH$_2$
LG = Cl, Br or S-alkyl

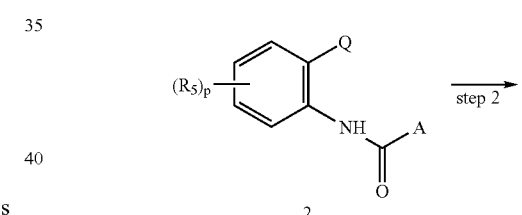

2

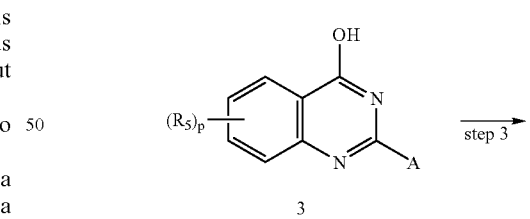

3

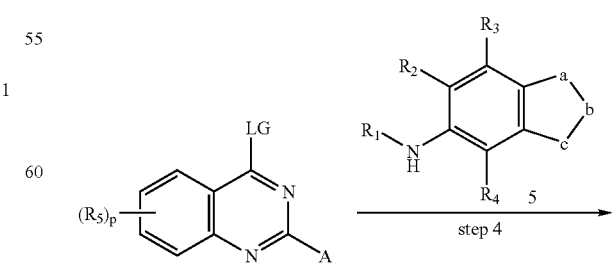

4

-continued

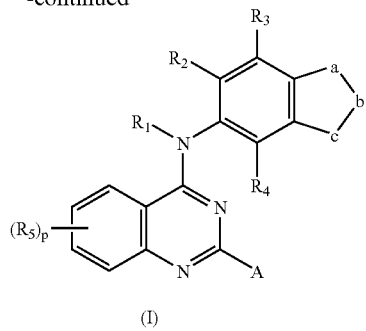

(I)

In this embodiment, a mixture of nitrile or amide 1 and an aliphatic or aromatic acid chloride (A-CO—Cl, commercially available, prepared beforehand from the carboxylic acid A-CO$_2$H, or prepared from the carboxylic acid in situ) are coupled, in the presence of a base such as a dialkylamine, DMAP, pyridine and the like. The nitriles and amides are readily available commercially, or if necessary, prepared from the corresponding anthranilic acid or anthranilic acid ester by straightforward means. The acid chlorides, A-CO—Cl starting materials, where not readily available commercially may be by standard preparatory methods from the corresponding carboxylic acids(using chlorinating reagents such as SOCl$_2$, phosgene or oxalyl chloride, with the optional addition of DMF (Hamuro et al. J. Am. Chem. Soc. 1996, 118(32), 7529-41). In instances where the carboxylic acid is not commercially available, it may be prepared by standard methods (Buerstinghaus et al. EP 203607, Dec. 3, 1986; Cai et al J. Chem Soc. Perkin Trans. I 1997, 16, 2273-74; von Geldern et al J. Med. Chem.1999, 42(18), 3668-78) such as oxidation of a suitable precursor, such as the corresponding hydroxymethyl-, or methyl-substituted compound (i.e., A-CH$_2$OH or A-CH$_3$), carboxylation of the corresponding halo compound (i.e., A-Cl, A-Br, or A-I) using palladium catalaysts, or quenching of a Grignard reagent (prepared from the corresponding halo compound (A-Cl, A-Br, or A-I) with carbon dioxide.

The Formula 2 product of may then be cyclized to the heterocycle of Formula 3 in the presence of a base such as aqueous sodium hydroxide, and is facilitated by heating to a temperature sufficient to effect the cyclization, typically, 40-95° C. In the instance where compound is a nitrile, the reaction mixture also contains H$_2$O$_2$ (usually in about 3-30% concentration), or alternatively, is conducted in 0.1 to 3.0 N mineral acid. The compound of Formula 3 is then converted to a compound of Formula 4 by treatment with a reagent such as SOCl$_2$, POCl$_3$/PCl$_5$, POCl$_3$, POBr$_3$ or P$_2$S$_5$/Et I (two steps) and is facilitated by the addition of a catalytic amount of DMF and heating. The compound of Formula 4 is then allowed to react in a water-miscible solvent such as DME, THF or DMF, with the amino heterocycle of Formula 5, in the presence of a base such as sodium or potassium acetate, potassium carbonate; or in dilute, (0.1M) hydrochloride acid, and water and with heating sufficient to effect reaction. In cases where the starting material 4 is especially labile, undesired side reactions (e.g., hydrolysis of 4 to 3 are minimized by reducing the amount of water added to water-miscible cosolvent to the minimum amount required to achieve dissolution and reaction.

It is to be understood that the specific conditions selected from this General Method will depend on the particular structures of the starting materials chosen, in order to optimize the yield of the products desired.

In Formula I, suitable aryl or heteroaryl groups, e.g., for A, include, but are not limited to, 5-12 carbon-atom aromatic rings or ring systems containing 1-3 rings, at least one of which is aromatic, in which one or more, e.g., 1-4 carbon atoms in one or more of the rings can be replaced by oxygen, nitrogen or sulfur atoms. Each ring typically has 3-7 atoms. For example, aryl or heteroaryl can be 2- or 3-furyl, 2- or 3-thienyl, 2- or 4-triazinyl, 1-, 2- or 3-pyrrolyl, 1-, 2-, 4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, 1,2,3-triazol-1-, -4- or 5-yl, 1,2,4-triazol-1-, -3- or B5-yl, 1- or 5-tetrazolyl, 1,2,3-oxadiazol-4- or 5-yl, 1,2,4-oxadiazol-3- or 5-yl, 1,3,4-thiadiazol-2- or 5-yl, 1,2,4-oxadiazol-3- or 5-yl, 1,3,4-thiadiazol-2- or 5-yl, 1,3,4-thiadiazol-3- or 5-yl, 1,2,3-thiadiazol-4- or 5-yl, 2-, 3-, 4-, 5- or 6-2H-thiopyranyl, 2-, 3- or 4-4H-thiopyranyl, 3- or 4-pyridazinyl, pyrazinyl, 2-, 3-, 4-, 5-, 6- or 7-benzofuryl, 2-, 3-, 4-, 5-, 6- or 7-benzothienyl, 1-, 2-, 3-, 4-, 5-, 6- or 7-indolyl, 1-, 2-, 4- or 5-benzimidazolyl, 1-, 3-, 4-, 5-, 6- or 7-benzopyrazolyl, 2-, 4-, 5-, 6- or 7-benzoxazolyl, 3-, 4-, 5- 6- or 7-benzisoxazolyl, 1-, 3-, 4-, 5-, 6- or 7-benzothiazolyl, 2-, 4-, 5-, 6- or 7-benzisothiazolyl, 2-, 4-, 5-, 6- or 7-benz-1,3-oxadiazolyl, 2-, 3-, 4-, 5-, 6-, 7- or 8-quinolinyl, 1-, 3-, 4-, 5-, 6-, 7-, 8-isoquinolinyl, 1-, 2-, 3-, 4- or 9-carbazolyl, 1-, 2-, 3-, 4-, 5-, 6-, 7-, 8- or 9-acridinyl, or 2-, 4-, 5-, 6-, 7- or 8-quinazolinyl, or additionally optionally substituted phenyl, 2- or 3-thienyl, 1,3,4-thiadiazolyl, 3-pyrryl, 3-pyrazolyl, 2-thiazolyl or 5-thiazolyl, etc.

Preferred moieties A include cyclohexyl; or C$_{5-12}$-aryl or C$_{5-12}$-heteroaryl each independently optionally substituted up to three times by (i) C$_1$-C$_{10}$-alkyl or C$_{2-10}$-alkenyl each optionally substituted with halogen up to perhalo; (ii) C$_3$-C$_{10}$ cycloalkyl; (iii) C$_{5-12}$-aryl optionally substituted by 1-3 halogen atoms; (iv) C$_{5-12}$-heteroaryl; (v) halogen; (vi) —CO—OR$_8$; (vii) —CO—R$_8$; (viii) cyano; (ix) —OR$_8$; (x) —NR$_8$R$_{13}$; (xi) nitro; (xii) —CO—NR$_8$R$_9$; (xiii) —C$_{1-10}$-alkyl-NR$_8$R$_9$; (xiv) —NR$_8$—CO—R$_{12}$; (xv) —NR$_8$—CO—OR$_9$; (xvi) —NR$_8$—SO$_2$—R$_9$; (xvii) —SR$_8$; (xviii) —SO$_2$—R$_8$; (xix) —SO$_2$—NR$_8$R$_9$, or (xx) NR$_8$—CO—NHR$_9$.

Further preferred moieties A include phenyl, pyridyl, pyrimidinyl, oxazolyl, furyl, thienyl, pyrrolyl, imidazolyl, isoxazolyl and pyrazinyl, each independently substituted up to three times by halogen, C$_{1-10}$-alkyl, C$_{1-10}$-alkoxyphenyl, naphthyl, —OR$_{10}$,

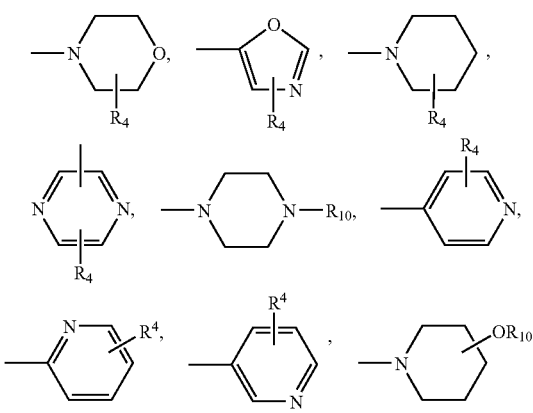

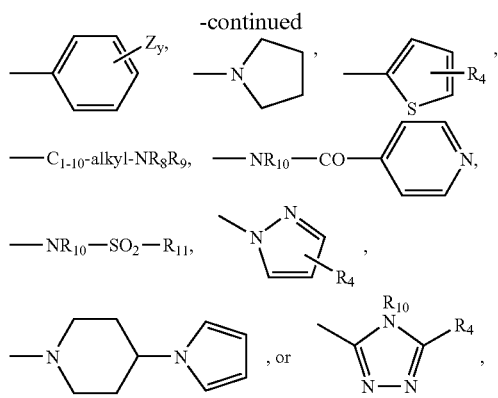

wherein each Z independently is halogen, hydroxy, hydroxy-$C_{1-10}$-alkyl, —CN, —NO$_2$, $C_{1-10}$-alkoxycarboxyl, —NR$_{10}$—CO—R$_{11}$, or —NR$_{10}$—CO—OR$_{11}$, y is 1-3, and R$_4$ is as described above.

Preferred moieties A additionally include

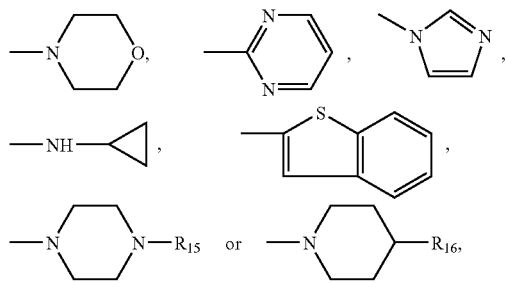

wherein R$_{15}$ is H; phenyl optionally substituted by $C_{1-10}$-alkyl, $C_{1-10}$-alkoxy, $C_{1-10}$-alkylcarboxyl, or halogen; benzyl; pyrimidyl or pyridyl; and R$_{16}$ is H, phenyl, —COOR$_{10}$,

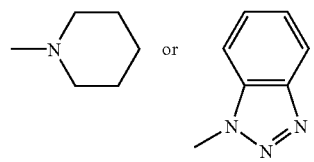

The terms identified above have the following meaning throughout:

"$C_{1-6}$ alkyl" means straight or branched chain alkyl groups having from one to about six carbons. Such groups include methyl, ethyl, n-propyl, isopropyl, n-butyl, isobutyl, sec-butyl, tert-butyl, n-pentyl, neo-pentyl, 2-pentyl, n-hexyl, 2-hexyl, 3-hexyl, 2,3-dimethylbutyl, and the like.

"$C_{1-10}$ alkyl" means straight or branched chain alkyl groups having from one to about ten carbon atoms.

"$C_{3-8}$ cycloalkyl" means saturated monocyclic alkyl groups of from 3 to about 8 carbon atoms and includes such groups as cyclopropyl, cyclopentyl, cyclohexyl, and the like.

"$C_{3-10}$ cycloalkyl" means saturated monocyclic alkyl groups of from 3 to about 10 carbon atoms.

"$C_{1-6}$ alkoxy" means straight or branched chain alkoxy groups having from one to about six carbon atoms and includes such groups as methoxy, ethoxy, n-propoxy, isopropoxy, n-butoxy, isobutoxy, sec-butoxy, tert-butoxy, and the like.

"Halo" means fluoro, chloro, bromo, or iodo.

"Mineral Acid" means hydrochlorine acid, sulfuric acid, nitric acid, and the like.

When an alkyl, cycloalkyl, alkenyl, or alkoxy group is described as being substituted with fluoro, it may be substituted with one or more fluorine atoms at any available carbon atom up to the perfluoro level.

When an alkyl substituent is described as being substituted by oxo, it means substitution by a doubly bonded oxygen atom, which forms together with the carbon to which it is attached, a carbonyl group —(C=O)—.

When any moiety is described as being substituted, it can have one or more of the indicated substituents that can be located at any available position on the moiety. When there are two or more substituents on any moiety, each substituent is defined independently of any other substituent and can, accordingly, be the same or different.

The term "optionally substituted" means that the moiety so modified may be unsubstituted or substituted with the identified substituent(s).

R$_5$ may be attached to the benzo moiety of the compounds of Formulas 1, 2, 3, 4, or (I), at any available carbon atom and when there are two or more R$_5$ substituents (i.e., p=2 or 3), each substituent is defined independently of other substituents and can, accordingly be the same or different.

"Aqueous hydroxide" means an aqueous solution containing OH$^-$, usually prepared from al.

"Water-miscible cosolvent" means an organic solvent which is at least partially miscible with water at a temperature in which the reaction is carried out. Such solvents include but are not limited to alcohols such as methanol, ethanol, isopropanol, butanol, methoxyethanol and the like, ethers such as dimethoxyethane (DME), tetrahydrofuran (THF), dioxane and the like, non-protic solvents such as N,N-dimethylformamide (DMF), and dimethylsulfoxide (DMSO), and solvents which may form an azeotrope with water such as toluene.

"Non-nucleophilic amine base" means a base capable of reacting with or neutralizing an acid, without the tendency to undergo nucleophilic substitution reactions. Such bases include diazabicycloundecane, 4-dimethylaminopyridine, "Non-protic solvent" means a solvent that does not readily dissociate to provide a H$^+$ ion, i.e. contains no H atoms with a pKa of less than about 20. Examples of such solvents include dimethylformamide DMF, THF, ether, toluene, benzene, dimethoxyethane (DME), diglyme, dioxane, Sensitive or reactive substituents, on the compounds of Formulas 1, 2, 3, 4, 5 or (I) may need to be protected and deprotected during any of the above methods of preparation. Protecting groups in general may be added and removed by conventional methods well known in the art (see, e.g., T. W. Greene and P. G. M. Wuts, *Protective Groups in Organic Synthesis*; Wiley: New York, (1999)).

The present invention is also directed to the production of pharmaceutically acceptable salts of compounds of Formula I. Suitable pharmaceutically acceptable salts are well known to those skilled in the art and include basic salts of inorganic and organic acids, such as hydrochloric acid, hydrobromic acid, sulphuric acid, phosphoric acid, methanesulphonic acid, sulphonic acid, acetic acid, trifluoroacetic acid, malic acid, tartaric acid, citric acid, lactic acid, oxalic acid, succinic acid, fumaric acid, maleic acid, benzoic acid, salicyclic acid, phenylacetic acid, and mandelic acid. In addition, pharmaceutically acceptable salts include acid salts of inorganic bases, such as salts containing alkaline cations (e.g., Li$^+$, Na$^+$ or K⁺), alkaline earth cations (e.g., Mg⁺, Ca⁺ or Ba⁺), the ammonium cation, as well as acid salts of organic bases, including aliphatic and aromatic substituted ammonium, and quaternary ammonium cations, such as those arising from protonation or peralkylation of triethylamine, N,N-diethylamine, N,N-dicyclohexylamine, pyridine, N,N-dimethylaminopyridine (DMAP), 1,4-diazabiclo[2.2.2]octane (DABCO), 1,5-diazabicyclo[4.3.0]non-5-ene (DBN) and 1,8-diazabicyclo[5.4.0]undec-7-ene (DBU). Preparation of such salts can proceed via a final conventional step using a compound of Formula I, subsequent to the above preparation process.

Abbreviations and Acronyms

When the following abbreviations are used herein, they have the following meaning:

| | |
|---|---|
| Ac₂O | acetic anhydride |
| anhy | anhydrous |
| n-BuOH | n-butanol |
| t-BuOH | t-butanol |
| CD₃OD | methanol-d₄ |
| Celite ® | diatomaceous earth filter agent, ® Celite Corp. |
| CH₂Cl₂ | methylene chloride |
| CI-MS | chemical ionization mass spectroscopy |
| conc | concentrated |
| dec | decomposition |
| DME | dimethoxyethane |
| DMF | N,N-dimethylformamide |
| DMSO | dimethylsulfoxide |
| ELSD | evaporative light scattering detector |
| EtOAc | ethyl acetate |
| EtOH | ethanol (100%) |
| Et₂O | diethyl ether |
| Et₃N | triethylamine |
| HPLC ES-MS | high performance liquid chromatography-electrospray mass spectroscopy |
| NMM | 4-methylmorpholine |
| Ph₃P | triphenylphosphine |
| Pd(dppf)Cl₂ | [1,1'-bis(diphenylphosphino)ferrocene]dichloropalladium(II) |
| Pd(PPh₃)₄ | tetrakis(triphenylphosphine)palladiUm(0) |
| Pd(OAc)₂ | palladium acetate |
| P(O)Cl₃ | phosphorous oxychloride |
| RT | retention time (HPLC) |
| rt | room temperature |
| THF | tetrahydrofuran |
| TFA | trifluoroacetic acid |
| TLC | thin layer chromatography |

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and, all parts and percentages are by weight, unless otherwise indicated.

The entire disclosure of all applications, patents and publications, cited above or below, and of U.S. Provisional Application No. 60/315,341, filed Aug. 29, 2001, U.S. patent application Ser. No. 10/103,566, filed Mar. 22, 2002, U.S. patent application Ser. No. 10/103,565, filed Mar. 22, 2002, PCT Application No. PCT/US02/08659, filed Mar. 22, 2002, and PCT Application No. PCT/US02/08660, filed Mar. 22, 2002, are hereby incorporated by reference.

EXAMPLES

Example 1

Preparation of 3-fluoro-4-phenylbenzoic Acid

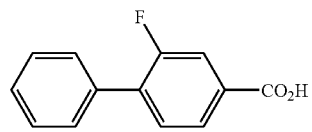

A suspension of magnesium (0.968 g, 3.98 mmol) and a few crystals of iodine in anhyd THF (200 mL) were treated with dropwise addition of 10 mL of a solution of 4-bromo-2-fluorobiphenyl (10.0 g, 3.98 mmol) in THF (100 mL). The mixture was heated to gentle reflux and a reaction ensued. At that time, the remaining solution of 4-bromo-2-fluorobiphenyl was added dropwise to the flask over a 3-minute period. The contents were then stirred at reflux under argon until no magnesium consumption was observed. The reaction mixture was subsequently cooled to −10° C. and treated with dry ice (~70 g). The reaction mixture was quenched with 20% aqueous hydrochloric acid (50 mL), and the layers were separated. The aqueous phase was extracted with ethyl acetate (2×20 mL), and the combined organic layer was washed with brine (30 mL), dried over anhyd sodium sulfate and concentrated to about ⅓ of its original volume. The contents were treated with hexane (200 mL), and the precipitate was filtered and dried under high vacuum to afford 3-fluoro-4-phenylbenzoic acid (6.37 g, 74%) as a white, crystalline solid. ¹H-NMR (DMSO-d₆): δ7.48 (m, 3H); 7.59 (m, 2H); 7.66 (dd, J=8.1, 8.1 Hz, 1H); 7.76 (dd, J=1.5, 11.6 Hz, 1H); 7.85 (dd, J=1.5, 8.1 Hz, 1H); 13.30 (br s, 1H). Anal. Calcd for C₁₃H₉FO₂: C, 72.22; H, 4.20; F, 8.79. Found: C, 71.95; H, 4.11; F, 9.07.

Example 2

Preparation of 2[(3-fluoro-4-phenylphenyl)carbonylamino]benzamide

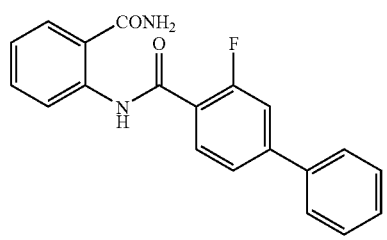

A suspension of the product of step 1 (0.5 g, 2.31 mmol) in oxalyl chloride (5 mL) was treated with one drop of DMF and the mixture was heated to 60° C. for 45 min. The resulting, clear-yellow solution was concentrated to a yellow solid, which was dried under high vacuum for 60 min. The solid and anthranilamide (0.314 g, 2.31 mmol) were suspended in dry toluene (5 mL), treated with diisopropylethylamine (0.5 ml, 0.371 g, 2.87 mmol) and the contents were stirred at room temperature for 2 h, at which time TLC (silica gel 60, 10% methanol/dichloromethane, UV detection) analysis suggested complete reaction. The mixture was filtered, and the off-white solid was dissolved in ethyl acetate (50 mL). The organics were washed with brine (25 mL), 0.1 N aqueous hydrochloric acid (25 mL), and again with brine (25 mL). The organic layer was dried over anhyd sodium sulfate, concentrated and dried under high vacuum for 4 h to afford the product (0.59 g, 1.76 mmol, 76%) as an off-white solid. $^1$H-NMR (DMSO-d$_6$): δ7.22 (ddd, J=1.2, 7.4, 7.8 Hz, 1H); 7.52 (m, 6H); 7.78 (m, 3H); 7.89 (m, 1H); 7.89, 8.47 (br s, 2H); 8.69 (dd, J=1.2, 8.3 Hz, 1H); 13.12 (s, 1H). Anal. Calcd for $C_{20}H_{15}N_2FO_2$: C, 71.85; H, 4.52; N, 8.38. Found: C, 71.67; H, 4.47; N, 8.35. Mass spectrum (HPLC/ES, flow injection): m/e=335(M+1).

Example 3

Preparation of 2-(3-fluoro-1,1'-biphenyl-4-yl)-4(3H)-quinazolinone

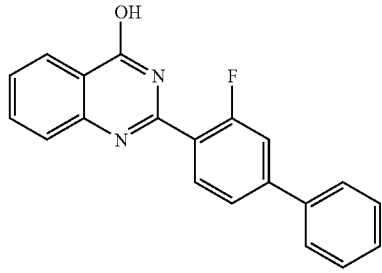

Method A (One Pot)

A suspension of the product of Example 1 (0.5 g, 2.31 mmol) in oxalyl chloride (5 mL) was treated with one drop of DMF and the mixture was heated to 60° C. for 60 min. The resulting clear yellow solution was concentrated to a yellow solid, which was dried under high vacuum for 2 h. This solid and anthranilamide (0.314 g, 2.31 mmol) were dissolved in dry THF (5 mL), treated with diisopropylethylamine (0.5 ml, 0.371 g, 2.87 mmol) and the contents were stirred at room temperature for 90 min, at which time TLC (silica gel 60, 5% methanol/dichloromethane, UV detection) analysis suggested complete reaction. The mixture was treated with aqueous 1.0 N sodium hydroxide (10.0 mL, 10.0 mmol). The contents were heated to 50° C. (complete dissolution occurred when the internal temperature reached 44° C.) for 90 min and the organic solvent was removed by rotary evaporation. The aqueous suspension was treated with dropwise addition of aqueous 2.0 N hydrochloric acid (about 5 mL) until the pH was adjusted to about 2. The precipitate was filtered and the cake was washed with water (4×30 mL) and dried under high vacuum at 40° C. for 18 h to provide the product (0.67 g, 2.12 mmol, 92%) as a white powder. $^1$H-NMR (DMSO-d$_6$): δ7.52 (m, 4H); 7.64 (m, 2H); 7.75 (m, 2H); 7.86 (ddd, J=1.4, 6.9, 8.0 Hz, 1H); 8.16 (m, 3H); 12.63 (br s, 1H). Anal. Calcd for $C_{20}H_{13}N_2FO$: C, 75.94; H, 4.14; N, 8.86. Found: C, 75.66; H, 4.29; N, 8.77. Mass spectrum (HPLC/ES): m/e=317(M+1).

Method B

A suspension of the product of Example 1 (0.5 g, 2.31 mmol) in oxalyl chloride (5 mL) was treated with one drop of DMF and the mixture was heated to 60° C. for 60 min. The resulting clear yellow solution was concentrated to a yellow solid, which was dried under high vacuum for 60 min. This solid and anthranilamide (0.314 g, 2.31 mmol) were suspended in dry toluene (5 mL), treated with diisopropylethylamine (0.5 ml, 0.371 g, 2.87 mmol) and the contents were stirred at room temperature for 2 h, at which time TLC (silica gel 60, 10% methanol/dichloromethane, UV detection) analysis suggested complete reaction. The mixture was filtered and dried under high vacuum for 2 h. The off-white solid was then dissolved in methanol (10 mL) and THF (5 mL), and the solution was treated with aqueous 1.0 N sodium hydroxide (10.0 mL, 10.0 mmol). The contents were heated to 45° C. for 2 h and the organic solvents were removed by rotary evaporation. The aqueous suspension was treated with dropwise addition of aqueous 2.0 N hydrochloric acid until the pH was adjusted to about 2 (5 mL). The precipitate was filtered and the cake was washed with water (4×30 mL) and dried under high vacuum at 40° C. for 3 h to provide product (0.66 g, 2.09 mmol, 90%) as a white powder. $^1$H-NMR (DMSO-d$_6$): δ7.52 (m, 4H, aromatic); 7.64 (m, 2H, aromatic); 7.75 (m, 2H); 7.86 (ddd, J=1.4, 6.9, 8.0 Hz, 1H, aromatic); 8.16 (m, 3H, aromatic); 12.63 (br s, 1H, —NH). Anal. Calcd for $C_{20}H_{13}N_2FO\cdot0.20$ $H_2O$: C, 75.08; H, 4.22; N, 8.76. Found: C, 75.08; H, 4.03; N, 8.67. Mass spectrum (HPLC/ES): m/e=317(M+1).

Method C

A solution of the compound of Example 2 (24.10 g, 72.08 mmol) in methanol (100 mL) and tetrahydrofuran 200 mL) was treated with aqueous 1.0 N sodium hydroxide (240 mL, 240 mmol), and the contents were stirred at 40° C. for 60 minutes, at which time TLC (silica gel 60, 10% methanol/dichloromethane, UV detection) analysis suggested complete reaction. The organic solvents were rotary evaporated and the aqueous phase was treated with dropwise addition of concentrated hydrochloric acid until the pH was adjusted to 7. The resultant white precipitate was filtered, washed with water (2×200 mL) and dried under high vacuum at room temperature for 2 days and at 45° C. for 2 hours to afford the product (21.60 g, 68.28 mmol, 95%) as a white powder. $^1$H-NMR (DMSO-d$_6$): δ7.50 (m, 4H, aromatic); 7.64 (m, 2H, aromatic); 7.74 (m, 2H); 7.86 (ddd, J=1.4, 6.9, 8.0 Hz, 1H, aromatic); 8.16 (m, 3H, aromatic); 12.63 (br s, 1H, —NH). Mass spectrum (HPLC/ES): m/e=317(M+1).

Method D

Step 1. Preparation of N-(2-cyanophenyl)(3-fluoro-4-phenylphenyl)carboxamide

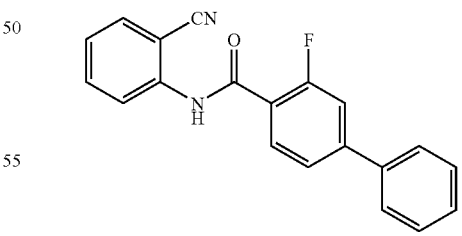

A suspension of the compound of Example 1 (0.5 g, 2.31 mmol) in oxalyl chloride (5 mL) was treated with one drop of N,N-dimethylformamide and the mixture was heated to 60° C. for 45 minutes. The resultant, clear-yellow solution was concentrated to a yellow solid, which was dried under high vacuum for 60 minutes. The solid and anthranilonitrile (13, 0.273 g, 2.31 mmol) were suspended in dry toluene (5 mL), treated with diisopropylethylamine (0.5 mL, 0.371 g, 2.87 mmol) and the contents were stirred at room temperature for 6 hours, at which time TLC (silica gel 60, 10% methanol/dichloromethane, UV detection) analysis suggested complete reaction. The mixture was filtered, and the white, crystalline solid was dissolved in 20% ethyl acetate/dichloromethane (25 mL). The organics were washed with 0.1 N aqueous hydrochloric acid (10 mL) and then with brine (2×25 mL). The organic layer was dried over sodium sulfate, concentrated and dried under high vacuum at 35° C. for 16 hours to afford 22 (0.49 g, 1.55 mmol, 67%) as a fluffy, white solid. $^1$H-NMR (DMSO-d$_6$): δ7.50 (m, 4H, aromatic); 7.62 (m, 3H, aromatic); 7.76 (m, 2H, aromatic); 7.92 (m, 3H, aromatic); 10.76 (s, 1H, —NH). Anal. Calcd for C$_{20}$H$_{13}$N$_2$FO: C, 75.94; H, 4.14; N, 8.86. Found: C, 75.71; H, 4.20; N, 8.92. Mass spectrum (HPLC/ES, flow injection): m/e=317(M+1).

Step 2. A sample of the product of step 1 (0.050 g, 0.158 mmol) was stirred in 1.5 M hydrochloric acid in ethanol (5 mL) at 40° C. for 60 minutes, at which time, TLC (silica gel 60, 20% EtOAc/hexane, UV detection) analysis indicated complete reaction. The contents were concentrated and then taken up in absolute ethanol (5 mL). The suspension was stirred, concentrated and the process was repeated two additional times. The material was dried under high vacuum at 45° C. for 2 hours to afford the product (0.047 g, 0.149 mmol, 94%) as a white powder. NMR analysis (see above) suggested that the compound was pure.

Example 4

Preparation of 4-chloro-2-(3-fluoro-4-phenylphenyl)quinazoline

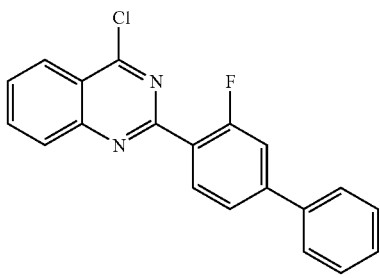

A solution of phosphorous oxychloride (3.0 mL) and anhyd DMF (2 mL) was stirred for 10 min before it was added to a flask containing the product of step 3 (0.300 g, 0.948 mmol). The resulting suspension was heated to gentle reflux under argon for 12 h. The dark solution was then cooled to 70° C. and slowly added to vigorously-stirred water (100 mL) at 0° C. A solid precipitated, which was stirred for 10 min and filtered. The cake was washed with water (2×25 mL) and dried under high vacuum at 35° C. for 2 h to provide product (0.285 g, 0.851 mmol, 90%) as a yellow solid. Part of this solid (0.125 g) was passed through a short plug of silica gel using 20% dichloromethane/hexane as eluant to afford the title compound (0.09 g) as white needles. $^1$H-NMR (DMSO-d$_6$): δ7.47 (m, 1H); 7.54 (m, 2H); 7.65 (m, 2H); 7.76 (dd, J=8.4, 8.4 Hz, 1H); 7.87 (ddd, J=2.9, 5.3, 8.3 Hz, 1H); 8.15 (m, 2H); 8.26 (m, 1H); 8.28 (m, 1H); 8.38 (dd, J=1.9, 8.4 Hz, 1H). Anal. Calcd for C$_{20}$H$_{12}$N$_2$ClF: C, 71.75; H, 3.61; N, 8.37; Cl, 10.59. Found: C, 71.54; H, 3.48; N, 8.29; Cl, 10.61. Mass spectrum (HPLC/ES): m/e=335(M+1). TLC (silica gel 60, 40% dichloromethane/hexane, UV detection): one spot, R$_f$=0.50.

Example 5

Preparation of 1H-indazol-5-yl[2-(3-fluoro-4-phenylphenyl)quinazolin-4-yl]amine

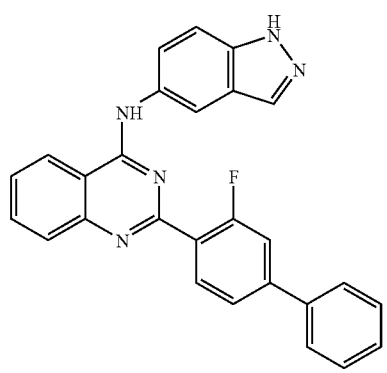

To a suspension of the product of step 4 (1.00 g, 2.99 mmol) and 5-aminoindazole (0.44 g, 3.29 mmol) in ethylene glycol dimethyl ether (DME, 10 mL) was added a solution of potassium acetate (0.44 g, 4.48 mmol) in water (2 mL). The contents were allowed to reflux for 16 h and then cooled to room temperature. The mixture was poured into water (200 mL) and the precipitate was filtered, washed with water (2×50 mL) and air-dried for 60 min. The solid was dissolved in THF (30 mL), and the solution was slowly poured into hexane (500 mL). The resulting precipitate was filtered and dried under high vacuum at 60° C. for 18 h to afford the product (1.02 g, 2.36 mmol, 79%) as a yellow solid. $^1$H-NMR (DMSO-d$_6$): δ7.46 (m, 3H, aromatic); 7.63 (m, 5H, aromatic); 7.83 (dd, J=1.9, 9.0 Hz, 1H, aromatic); 7.87 (m, 2H, aromatic); 8.13 (br s, 1H, —N=CH—); 8.17 (dd, J=1.6, 12.5 Hz, 1H, aromatic); 8.22 (d, J=1.9 Hz, 1H, aromatic); 8.30 (dd, J=1.6, 8.0 Hz, 1H, aromatic); 8.58 (br d, J=8.5 Hz, 1H, aromatic); 10.04 (s, 1H, —NH); 13.13 (br s, 1H, —NH). Mass spectrum (HPLC/ES): m/e=432(M+1).

In order to prepare the p-toluene sulfonic acid (tosylate) salt, a suspension of the product (0.60 g, 1.39 mmol) in anhyd ethanol (12 mL) was treated with a solution of p-toluenesulfonic acid monohydrate (0.39 g, 2.09 mmol) in ethanol (8.5 mL) in one portion. The contents were stirred at 40° C. for 60 min and the precipitate was filtered. The cake was washed with ethanol (3×15 mL) and dried under high vacuum at 40° C. for 18 h to give the tosylate salt (0.71 g, 85%) as a pale-orange, crystalline solid. $^1$H-NMR (DMSO-d$_6$): δ2.27 (s, 3H); 7.09, 7.47 (AA'BB' quartet, J=8.6 Hz, 4H); 7.48 (m, 2H); 7.52 (m, 2H); 7.62 (m, 2H); 7.73 (m, 2H); 7.84 (m, 2H); 8.10 (m, 5H); 8.20 (s, 1H); 8.74 (br d, J=8.4 Hz, 1H); 11.50 (br s, 1H). Anal. Calcd for C$_{27}$H$_{18}$N$_5$F.CH$_3$C$_6$H$_4$SO$_3$H: C, 67.65; H, 4.34; N, 11.60. Found: C, 67.35; H, 4.46; N, 11.49. Mass spectrum (HPLC/ES): m/e=432(M+1).

Example 6

Preparation of N-[2-(aminocarbonyl)phenyl]-2,3-dihydro-1-benzofuran-5-carboxamide

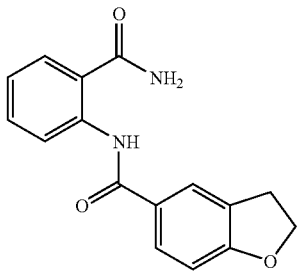

A mixture of 2,3-dihydrobenzo[b]furan-5-carboxylic acid (1.0 g, 6.1 mmol) in thionyl chloride (2.2 mL, 30.5 mmol) is stirred at room temperature for 4 h. The volatiles were removed by evaporation. To a solution of the residue and anthranilamide (750 mg, 5.5 mmol) in CHCl$_3$ (30 mL) is added pyridine (670 □L, 8.3 mmol) and the mixture stirred at room temperature for 18 h. The volatiles were removed by evaporation and the residue is partitioned between EtOAc and 1 N sodium carbonate. The resulting precipitate that formed between the aqueous and organic phases is collected by filtration and dried under vacuum to afford the desired intermediate (1.5 g, 5.3 mmol; 87% yield); ); Rf=0.31 (EtOAc/hexanes, 95/5); mp=230-235° C.; ES MS(M+H)$^+$=283.

Example 7

Preparation of 2-(2,3-dihydro-1-benzofuran-5-yl)-4-quinazolinol

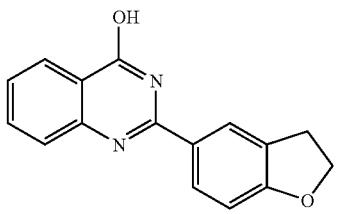

To a solution of diamide from Step 1 (1.0 g, 3.5 mmol) in EtOH (25 mL) is added 10 N NaOH (1.06 mL, 10.6 mmol). The reaction heated to reflux for 16 h, the mixture is cooled to room temperature and the volatiles were evaporated. The aqueous mixture is adjusted to pH=5 with conc HCl. The resulting precipitate is collected by filtration and dried under vacuum to afford the desired product: Rf=0.45 (EtOAc/hexanes, 95/5); (856 mg, 3.2 mmol; 91% yield); mp=289-294° C.; ES MS(M+H)$^+$=265.

Example 8

Preparation of 4-chloro-2-(2,3-dihydro-1-benzofuran-5-yl)quinazoline

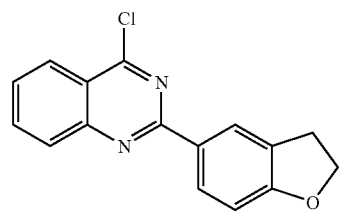

To a suspension of material from Step 2 (300 mg, 1.1 mmol) in CHCl$_3$ (12 mL) is added thionyl chloride (990 □L, 13.6 mmol) and DMF (20 □L, 0.3 mmol). The mixture heated to reflux for 4 h, cooled to room temperature, and the volatiles were evaporated. The residue is dried under vacuum to afford the desired intermediate (285 mg, 1.0 mmol; 89% yield); Rf=0.52 (EtOAc/hexanes, 80/20); mp=186-192° C.; ES MS(M+H)$^+$=283.

Example 9

Preparation of 2-(2,3-dihydro-1-benzofuran-5-yl)-N-(1H-indazol-5-yl)-4-quinazolinamine

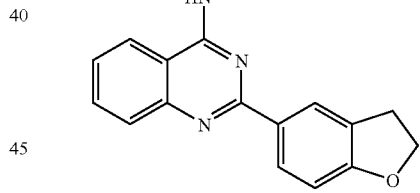

A mixture of Step 3 compound (100 mg, 0.35 mmol), 5-aminoindazole (47.1 mg, 0.35 mmol) and 0.1 M aqueous HCl (350 □L) heated at reflux temperature 16 h. The reaction cooled to room temperature and the solvent is evaporated in vacuo. The residue is triturated with MeOH and dried under vacuum to afford the product (43.4 mg, 0.11 mmol; 32% yield); Rf=0.57(CH$_2$Cl$_2$/MeOH, 90/10); mp=267-272° C.; ES MS(M+H)$^{30}$ =380.

Examples 10-11

By following a procedure analogous to that described for Example 6-9 and using the appropriate chloroquinazoline and 5-aminoindazole as starting materials, the compounds described in Table 1 were similarly prepared:

TABLE 1

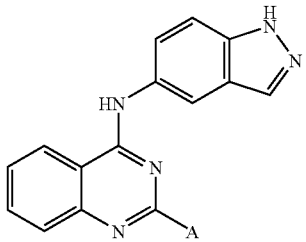

| Ex. No. | A | Weight obtained (mg) | Yield % | Note |
|---|---|---|---|---|
| 10 | cyc-Pr | 104.6 | 71 | 25 |
| 11 | $CF_3$ | 44.2 | 31 | 26 |

Notes:
25 Rf = 0.46 ($CH_2Cl_2$/MeOH, 90/10); mp = 272-277° C.; ES MS $(M + H)^+$ = 302.
26 Rf = 0.62 ($CH_2Cl_2$/MeOH, 90/10); mp = 311-319° C.; ES MS $(M + H)^+$ = 330.

Example 12

Preparation of N-(1H-indazol-5-yl)-2-(2-quinoxalinyl)-4-quinazolinamine

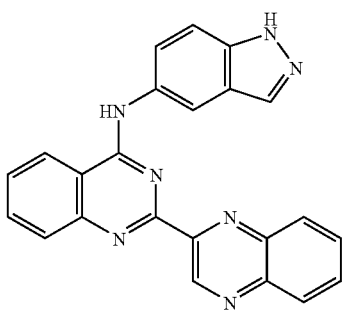

Step 1: To a solution of anthranilonitrile (7.58 mmol) in dry pyridine (30 mL) is added 2-quinoxaloyl chloride (9.11 mmol, 1.2 equivalent). The reaction mixture stirred at room temperature overnight and sodium hydroxide solution (2%, 50 mL) is added. The mixture is cooled and stirred for 30 min. The resulting white solid is collected by filtration, washed with brine and cold ether. A white solid product is obtained (1.51 g, 73%). HPLC/MS: $(M+H)^+$=275, RT (HPLC/MS)= 3.0 min.

Step 2: The amide prepared in Step 1 (9.5 mmol, 1 equiv) is suspended in dioxane (10 mL). NaOH solution (20%, 60 mL) and hydrogen peroxide solution (30%, 30 mL) is added in three portions. A vigorous release of gas is observed. The reaction mixture continued to stir and is cooled when necessary until the evolution of gas ceased. The reaction is brought to 120° C. (oil bath) and stirred overnight at this temperature. The reaction is neutralized with concentrated HCl to pH=7. A precipitate formed and is collected on a funnel, washed with water and dried in vacuo. A yellow solid is obtained and used in the next step without further purification. HPLC/MS: $(M+H)^+$=275, RT(HPLC/MS)=3.28.

Step 3: The quinazoline (10.9 mmol) is suspended in phosphorous oxychloride (214.6 mmol) containing $PCl_5$ (10.9 mmol) and stirred at 115° C. for 18 h. The resulting yellow solution is poured into 300 mL of ice and stirred. A gray precipitate formed and filtered and washed with cold water. The product is used in the next step without further purification. HPLC/MS: $(M+H)^+$=293, RT(LC-MS)=3.40.

Step 4: A mixture of 4-chloroquinazoline, potassium acetate (14.25 mmol), and 5-aminoindazole (10.96 mmol) in THF/$H_2O$ (70 mL/25 mL) is stirred at room temperature for 17 h. The resulting solid is collected by filtration and purified by silica gel column chromatography (gradient, 5-10% MeOH/$CH_2Cl_2$) to afford the product (1.19 g, 32%, 3 steps) as yellow powder. HPLC/MS: $(M+H)^+$=390, RT(LC-MS)= 2.41.

Example 13

Preparation of 5-Fluoro-N-(1H-indazol-5-yl)-2-(2-methylphenyl)-4-quinazolinamine

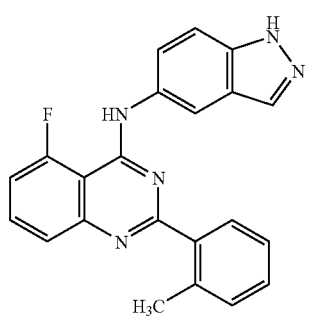

Step 1: To a solution of 6-fluoro-2-amino-benzonitrile (2 mmol, 1 equivalent.) in pyridine (3 mL) and $CH_2Cl_2$ (1 mL) containing N-dimethylaminopyridine (3 mg) is added 2-toluoyl chloride (316 mL, 1.2 equivalent). The reaction mixture is shaken at room temperature for 48 h and poured into cold water (3 mL) and shaken for 1 h. The resulting solid is filtered and washed with water to afford a white solid (90%). The LC-MS is consistent with the desired compound.

Step 2: The product is suspended in aqueous NaOH (20%, 2 mL) and dioxane (1 mL). Hydrogen peroxide (30%, 1 mL) is added in potions to avoid vigorous formation of gas. The reaction is shaken at 85° C. for 20 h and then is neutralized with acetic acid to pH=7. The resulting precipitate is collected by filtration, washed with water and ether, and dried over $P_2O_5$ for two days. The product is suspended in P(O)$Cl_3$ (4 mL) and shaken at 90° C. overnight. The $POCl_3$ is removed in vacuo and co-evaporated with toluene. The resulting yellow solid residue is dried in vacuo overnight and used in the next step without further purification Step 3: The product (assumed to be 2 mmol), 5-aminoindazole (3 mmol, 1.5 equiv), and potassium carbonate (2 mmol) were suspended in DMF (5 mL) containing and shaken at 90° C. for 24 h. The reaction suspension is filtered and the filtrate is purified by HPLC, under the following conditions:

Column: YMC C18 Pro, 20×150 m/m; Gradient: A=H2O, 0.1% TFA, B=$CH_3CN$, 0.1% TFA; Gradient over 10 min, flow: 30 mL/min. A pale yellow solid product is obtained. $(M+H)^+$=370, RT(LC-MS)=2.19 min.

Using the method described above for Example 13 and substituting the appropriate starting materials, the compounds listed in Table 2 were also synthesized.

TABLE 2

| Example No | (R$_5$) | A | LC-MS RT (min) | Mass Spec |
|---|---|---|---|---|
| 14 | 5-F | 4-fluorophenyl | 2.67 | 374 |
| 15 | 5-F | 3-chlorophenyl | 3.14 | 350 |
| 16 | 5-F | 4-bromophenyl | 3.09 | 434 |
| 17 | 5-F | 3-methylphenyl | 2.56 | 370 |
| 18 | 5-F | 3-bromophenyl | 3.18 | 434 |
| 19 | 5-F | 2-chlorophenyl | 2.52 | 390 |
| 20 | 5-F | 3-methoxyphenyl | 2.52 | 386 |
| 21 | 5-F | 2-quinoxalinyl | 2.48 | 408 |
| 22 | 5-F | 1-naphthyl | 2.48 | 406 |
| 23 | 5-F | 2-naphthyl | 2.96 | 406 |
| 24 | 5-F | 4-pyridinyl | 2.3 | 357 |
| 25 | 7-methyl | 2-quinoxalinyl | 2.37 | 404 |
| 26 | 7-methyl | 3-chlorophenyl | 2.56 | 386 |
| 27 | 7-methyl | 4-fluorophenyl | 2.30 | 370 |
| 28 | 7-methyl | 4-methylphenyl | 2.41 | 366 |
| 29 | 7-methyl | 4-bromophenyl | 2.59 | 430 |
| 30 | 7-methyl | 4-methoxyphenyl | 2.30 | 382 |
| 31 | 7-methyl | 2-methylphenyl | 2.26 | 366 |
| 32 | 7-methyl | 3-methylphenyl | 2.41 | 366 |
| 33 | 7-methyl | 3-fluorophenyl | 2.48 | 370 |
| 34 | 7-methyl | 3-bromophenyl | 2.70 | 430 |
| 35 | 7-methyl | 2-chlorophenyl | 2.37 | 386 |
| 36 | 7-methyl | 3-methoxyphenyl | 2.44 | 382 |

Example 37

Preparation of 4-ethylthio-2-(3-fluoro-4-phenylphenyl)quinazoline

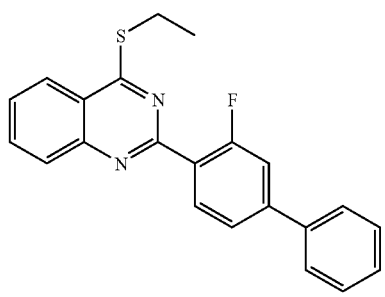

A mixture of Example 3 (2.0 g, 6.32 mmol) and phosphorous pentasulfide (0.560 g, 2.53 mmol) in pyridine (20 mL) was heated to 114° C. for 5 h, at which time TLC (silica gel 60, 10% MeOH/dichloromethane, UV detection) analysis indicated complete reaction. The contents were cooled to 60° C. and slowly added to vigorously-stirred water (50 mL) at 40° C. The mixture was stirred for 20 minutes, filtered and dried under high vacuum to provide 2-(3-fluoro-1,1'-biphenyl-4-yl)-4(3H)-quinazolinethione, 2.05 g, 6.17 mmol, 98%) as a yellow solid. A suspension of this material (0.500 g, 1.50 mmol) in dimethyl sulfoxide (4 mL) was treated with iodoethane (0.26 mL, 0.0507 g, 3.25 mmol) in one portion, followed by dropwise addition of aqueous sodium bicarbonate (1.6 mL). The mixture was stirred at room temperature for 16 hours, slowly poured into vigorously-stirred water (30 mL) and filtered. The resultant cake was dried under high vacuum at 40° C. for 15 hours to afford 4-ethylthio-2-(3-fluoro-4-phenylphenyl)quinazoline (0.471 g, 1.31 mmol, 87%) as a pale-yellow solid. $^1$H-NMR (DMSO-d$_6$): δ1.48 (t, J=7.4 Hz, 3H, —CH$_2$CH$_3$); 3.51 (q, J=7.4 Hz, 2H, —CH$_2$CH$_3$); 7.50 (m, 3H, aromatic); 7.69 (m, 4H, aromatic); 7.99 (m, 2H, aromatic); 8.09 (m, 1H aromatic); 8.33 (dd, J=1.7, 12.3 Hz, 1H, aromatic); 8.45 (dd, 1H J=1.7, 8.0 Hz, aromatic). Mass spectrum (HPLC/ES): m/e=361(M+1).

Example 38

Preparation of 1H-indazol-5-yl[2-(3-fluoro-4-phenylphenyl)quinazolin-4-yl]amine from Example 37

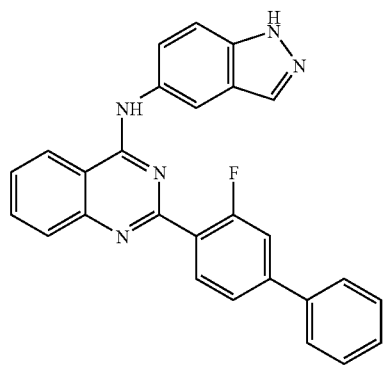

A solution of 5-aminoindazole (0.020 g, 0.15 mmol) in dry N,N-dimethylformamide (4 mL) was added dropwise to a solution of potassium t-butoxide (0.017 g, 0.15 mmol) in dry N,N-dimethylformamide (1 mL). The reaction mixture went from green to red within a 20-minute period, and the contents were stirred at room temperature for 1 hour before the flask was treated with a solution of the compound of Example 37 (0.050 g, 0.14 mmol) in dry N,N-dimethylformamide (2 mL). The contents were stirred at room temperature for 2 hours, at which time TLC (silica gel 60, 5% methanol/dichloromethane, UV detection) analysis indicated complete consumption of starting quinazoline. The reaction mixture was poured into ethyl acetate (20 mL), and the organics were washed with brine (20 mL, 3×30 mL), dried over sodium sulfate and concentrated. The material was air-dried for 2 hours to give the product (0.031 g, 51%) as a pale-green solid. The NMR data was identical to that obtained in Example 5.

The entire disclosure of all applications, patents and publications, cited above or below, corresponding U.S. Provisional Application Serial No. 60/277,974, filed Mar. 23, 2001, U.S. Provisional Application No. 60/315,341, filed Aug. 29, 2001, U.S. Provisional Application Serial No. 60/315,388, filed Aug. 29, 2001, U.S. application Ser. No. 10/103,565, filed Mar. 22, 2002, U.S. application Ser. No. 10/103,566, filed Mar. 22, 2002, International Patent Application No. PCT/US02/08659 filed Mar. 22, 2002, and International Patent Application No. PCT/US02/08660 filed Mar. 22, 2002, are hereby incorporated by reference.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

We claim:

1. A process for the preparation of a compound of Formula (I)

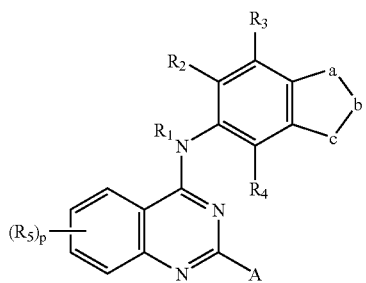

comprising reacting a compound of Formula 4'

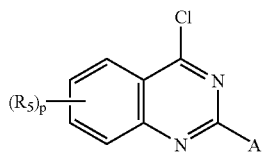

and a compound of Formula 5

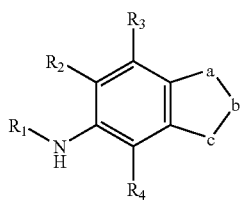

wherein a and c are each independently —$CR_5$= or —$NR_6$—, wherein one of a or c is —$NR_6$—;

b is —N=;

A is a 3-20 atom, cyclic or polycyclic moiety, which optionally contain 1-3 N, O or S atoms per ring, and may optionally be aryl or heteroaryl, which cyclic or polycyclic moiety may optionally be substituted up to 3 times by (i) $C_1$-$C_{10}$ alkyl or $C_2$-$C_{10}$-alkenyl, each optionally substituted with halogen up to perhalo; (ii) $C_3$-$C_{10}$cycloalkyl; (iii) aryl; (iv) heteroaryl; (v) halogen; (vi) —CO—$OR_8$; (vii) —CO—$R_8$; (viii) cyano; (ix) —$OR_8$, (x) -$NR_8R_{13}$; (xi) nitro; (xii) —CO—$NR_8R_9$; (xiii) -$C_{1-10}$-alkyl-$NR_8R_9$; (xiv) —$NR_8$—CO—$R_{12}$; (xv) —$NR_8$—CO—$OR_9$; (xvi) —$NR_8$—$SO_2$—$R_9$; (xvii) —$SR_8$; (xviii) —$SO_2$—$R_8$; (xix) —$SO_2$—$NR_8R_9$; or (xx) $NR_8$—CO—$NHR_9$;

$R_1$, $R_6$ and $R_8$ -$R_{11}$ are each independently H or $C_{1-6}$ alkyl;

$R_2$, $R_3$ and $R_4$ are each independently (i) $C_{1-10}$ alkyl or $C_{2-10}$-alkenyl each optionally substituted by amino, N-lower alkylamino, N,N-dilower alkylamino, N-lower alkanoylamino, hydroxy, cyano, —$COOR_{10}$, —$COR_{14}$, —$OCOR_{14}$, —$OR_{10}$, $C_{5-10}$-heteroaryl, $C_{5-10}$-heteroaryloxy, or $C_{5-10}$-heteroaryl-$C_{1-10}$-alkoxy, halogen up to perhalo; (ii) $C_3$-$C_{10}$ cycloalkyl, in which 1-3 carbon atoms are optionally independently replaced by O, N or S; (iii) $C_{3-10}$-cycloalkenyl; (iv) partially unsaturated $C_{5-10}$-heterocyclyl; (v) aryl; (vi) heteroaryl; (vii) halogen; (viii) —CO—$OR_{10}$; (ix) —$OCOR_{10}$; (x) —$OCO_2R_{10}$; (xi) —CHO; (xii) cyano; (xiii) —$OR_{16}$; (xiv) —$NR_{10}R_{15}$; (xv) nitro; (xvi) —CO—$NR_{10}R_{11}$; (xvii) —$NR_{10}$—CO—$R_{12}$; (xviii) —$NR_{10}$—CO—$OR_{11}$; (xix) —$NR_{10}$—$SO_2$—$R_{12}$; (xx) —$SR_{16}$; (xxi) —$SOR_{16}$; (xxii) —$SO_2$—$R_{16}$; (xxiii) —$SO_2$—$NR_{10}R_{11}$; (xxiv) $NR_{10}$—CO—$NHR_{11}$; (xxv) amidino; (xxvi) guanidino; (xxvii) sulfo; (xxviii) —$B(OH)_2$; (xxix) —$OCON(R_{10})_2$; or (xxx) —$NR_{10}CON(R_{10})_2$;

$R_5$ is independently (i) $C_{2-10}$-alkenyl, optionally substituted by amino, N-lower alkylamino, N,N-dilower alkylamino, N-lower alkanoylamino, hydroxy, cyano, —$COOR_{10}$, —$COR_{14}$ or —$OCOR_{14}$, —$OR_{10}$, $C_{5-10}$-heteroaryl, $C_{5-10}$-heteroaryloxy, or $C_{5-10}$-heteroaryl-$C_{1-10}$-alkoxy, halogen up to perhalo; (ii) $C_3$-$C_{10}$ cycloalkyl, in which 1-3 carbon atoms are optionally independently replaced by O, N or S; (iii) $C_{3-10}$-cycloalkenyl; (iv) partially unsaturated $C_{5-10}$-heterocyclyl; (v) aryl; (vi) heteroaryl; (vii) —CO—$OR_{10}$; (viii) —$OCOR_{10}$; (ix) —$OCO_2R_{10}$; (x) —CHO; (xi) cyano; (xii) —$NR_{10}R_{15}$; (xiii) —CO—$NR_{10}R_{11}$; (xiv) —$NR_{10}$—CO—$R_{12}$; (xv) —$NR_{10}$—CO—$OR_{11}$; (xvi) —$NR_{10}$—$SO_2$—$R_{12}$; (xvii) —$SR_{16}$; (xviii) —$SOR_{16}$; (xix) —$SO_2$—$R_{16}$; (xx) —$SO_2$—$NR_{10}R_{11}$; (xxi) $NR_{10}$—CO—$NHR_{11}$; (xxii) amidino; (xxiii) guanidino; (xxiv) sulfo; (xxv) —$B(OH)_2$; (xxvi) —$OCON(R_{10})_2$; or (xxvii) —$NR_{10}CON(R_{10})_2$.

$R_{12}$ is H, $C_{1-6}$-alkyl or $C_{5-10}$-aryl, $R_{13}$ is H, $C_{1-6}$-alkyl or $C_{1-6}$-alkoxy, $R_{14}$ is lower alkyl or phenyl;

$R_{15}$ is lower alkyl, halogen, amino, N-lower alkyl amino, N,N-dilower alkylamino, N-lower alkanoylamino, OH, CN, $COOR_{10}$, —$COR_{14}$ or —$OCOR_{14}$;

$R_{16}$ is hydrogen, $C_{1-6}$-alkyl optionally substituted by halogen, up to perhalo, or $C_{5-10}$-heteroaryl; and p=0,1,2 or 3;

with the proviso that compound I is not

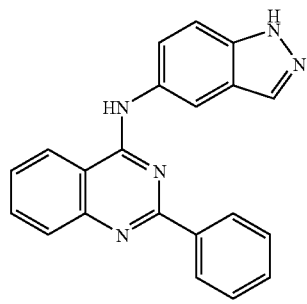

and formula 4' is not 4,7-dichloro-2-phenylquinazoline.

* * * * *

UNITED STATES PATENT AND TRADEMARK OFFICE
CERTIFICATE OF CORRECTION

PATENT NO. : 7,645,878 B2  Page 1 of 1
APPLICATION NO. : 10/252369
DATED : January 12, 2010
INVENTOR(S) : Bankston et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1691 days.

Signed and Sealed this

Sixteenth Day of November, 2010

David J. Kappos
*Director of the United States Patent and Trademark Office*